United States Patent
Lerner et al.

(10) Patent No.: US 6,531,152 B1
(45) Date of Patent: *Mar. 11, 2003

(54) IMMEDIATE RELEASE GASTROINTESTINAL DRUG DELIVERY SYSTEM

(75) Inventors: E. Itzhak Lerner, Petah Tikva (IL); Moshe Flashner, Petah Tikva (IL); Adel Penhasi, Bat Yam (IL)

(73) Assignee: Dexcel Pharma Technologies Ltd., Hadera (IL)

(*) Notice: Subject to any disclaimer, the term of this patent is extended or adjusted under 35 U.S.C. 154(b) by 0 days.

This patent is subject to a terminal disclaimer.

(21) Appl. No.: 09/694,314

(22) Filed: Oct. 24, 2000

Related U.S. Application Data

(63) Continuation of application No. 09/163,202, filed on Sep. 30, 1998, now abandoned.

(51) Int. Cl.[7] ................................................. A61K 9/20
(52) U.S. Cl. .................... 424/464; 424/465; 424/468; 424/471; 424/473; 424/474; 424/977; 424/479; 424/482; 424/489
(58) Field of Search ................................. 424/464, 465, 424/468, 471, 473, 474, 477, 479–482, 848–489

(56) References Cited

U.S. PATENT DOCUMENTS

| | | |
|---|---|---|
| 3,921,636 A | 11/1975 | Zaffaroni |
| 4,106,100 A | 8/1978 | Okada et al. |
| 4,107,288 A | 8/1978 | Oppenheim et al. |
| 4,138,362 A | 2/1979 | Vassiliades et al. |
| 4,169,804 A | 10/1979 | Yapel, Jr. |

(List continued on next page.)

FOREIGN PATENT DOCUMENTS

| | | |
|---|---|---|
| CA | 2020802 | 1/1991 |
| EP | 0077 956 | 4/1983 |
| EP | 077 956 | 5/1983 |

(List continued on next page.)

OTHER PUBLICATIONS

Kwan et al, "Pharmacokinetics of Sulindac", *Acta Rhum Belgica*, 1:168–178, 1977.

Adkin et al, The Use of Scintigraphy to Provide "Proof of Concept" for Novel Polysaccharide Preparations Designed for Colonic Drug Delivery, *Pharm Res*, 14(1):103–107, 1997.

Bedi et al, "Inhibition of Apoptosis During Development of Colorectal Cancer", *Cancer Res*, 55(9):1811–1816, 1995.

(List continued on next page.)

*Primary Examiner*—Thurman K. Page
*Assistant Examiner*—Lakshmi Channavajjah
(74) *Attorney, Agent, or Firm*—D'vorah Graeser

(57) ABSTRACT

A gastrointestinal delivery system is provided. The system comprises a drug in combination with a swellable core material, the core being surrounded by a water-insoluble or relatively water-insoluble coating material in which particulate water-insoluble material is embedded. When the delivery device enters the gastrointestinal tract, the particulate matter takes up liquid, thus forming channels interconnecting the drug-containing core with the outside of the delivery device. Through these channels liquid enters the core which then swells to the point at which the coating is broken. When the integrity of the coating is destroyed, the core then disintegrates immediately releasing all or most of the drug at a specific site. By controlling parameters in the device, such as the core material, carrier material in the coating, and particulate matter, the location of release of the drug can be carefully controlled. Thus, the invention is also directed to a method of using the device for the treatment of disease by the release of drugs in the gastrointestinal tract in a location- and time-dependent manner.

44 Claims, 11 Drawing Sheets

U.S. PATENT DOCUMENTS

| | | | |
|---|---|---|---|
| 4,169,885 A | 10/1979 | Raaf et al. | |
| 4,227,364 A | 10/1980 | Scherbring | |
| 4,252,786 A | 2/1981 | Weiss et al. | |
| 4,279,812 A | 7/1981 | Cioca | |
| 4,307,717 A | 12/1981 | Hymes et al. | |
| 4,327,725 A | 5/1982 | Cortese et al. | |
| 4,344,857 A | 8/1982 | Horikoshi et al. | |
| 4,349,530 A | 9/1982 | Royer | |
| 4,359,483 A | 11/1982 | Kaetsu et al. | |
| 4,432,966 A | 2/1984 | Zeiton et al. | |
| 4,442,655 A | 4/1984 | Stroetmann | |
| 4,492,684 A | 1/1985 | Goosen et al. | |
| 4,568,536 A | 2/1986 | Kronenthal et al. | |
| 4,569,837 A | 2/1986 | Suzuki et al. | |
| 4,610,870 A | 9/1986 | Jain et al. | |
| 4,619,913 A | 10/1986 | Luck et al. | |
| 4,627,850 A | 12/1986 | Deters et al. | |
| 4,675,381 A | 6/1987 | Bichon | |
| 4,678,516 A | 7/1987 | Alderman et al. | |
| 4,703,108 A | 10/1987 | Silver et al. | |
| 4,794,002 A | 12/1988 | Henis et al. | |
| 4,803,075 A | 2/1989 | Wallace et al. | |
| 4,871,549 A | * 10/1989 | Ueda et al. | 424/494 |
| 4,891,223 A | 1/1990 | Ambegaonkar et al. | |
| 4,897,270 A | 1/1990 | Deutsch et al. | |
| 4,904,474 A | 2/1990 | Theeuwes | |
| 5,229,131 A | 7/1993 | Amidon et al. | |
| 5,260,069 A | 11/1993 | Chen | |
| 5,401,774 A | 3/1995 | Pamukcu et al. | |
| 5,422,121 A | 6/1995 | Lehmann et al. | |
| 5,464,633 A | 11/1995 | Conte et al. | |
| 5,472,708 A | 12/1995 | Chen | |
| 5,498,608 A | 3/1996 | Johnson et al. | |
| 5,514,663 A | 5/1996 | Mandel | |
| 5,525,634 A | 6/1996 | Sintov et al. | |
| 5,531,735 A | 7/1996 | Thompson | |
| 5,593,697 A | 1/1997 | Barr et al. | |
| 5,622,948 A | 4/1997 | Mandel et al. | |
| 5,643,959 A | 7/1997 | Pamukcu | |
| 5,651,983 A | 7/1997 | Kelm et al. | |
| 5,654,009 A | 8/1997 | Hata et al. | |
| 5,656,290 A | 8/1997 | Kelm et al. | |
| 5,679,638 A | 10/1997 | Teicher et al. | |
| 5,686,105 A | 11/1997 | Kelm et al. | |
| 5,686,106 A | 11/1997 | Kelm et al. | |
| 5,686,589 A | 11/1997 | Brendel et al. | |
| 5,688,776 A | * 11/1997 | Bauer et al. | 514/54 |
| 5,780,055 A | 7/1998 | Habib et al. | |
| 5,840,332 A | * 11/1998 | Lerner et al. | 424/464 |
| 5,874,418 A | 2/1999 | Stella et al. | |
| 6,231,888 B1 | * 5/2001 | Lerner et al. | 424/463 |

FOREIGN PATENT DOCUMENTS

| | | | |
|---|---|---|---|
| EP | 0077956 | * | 5/1983 |
| EP | 0 077 956 | | 5/1983 |
| EP | 0 210 540 | | 2/1987 |
| EP | 0 305 918 A | | 3/1989 |
| EP | 305 918 A1 | | 3/1989 |
| EP | 485 157 A2 | | 5/1992 |
| EP | 485 158 A2 | | 5/1992 |
| EP | 485 171 A2 | | 5/1992 |
| EP | 485 172 A2 | | 5/1992 |
| EP | 485 173 A2 | | 5/1992 |
| EP | 0 485 840 | | 5/1992 |
| EP | 0 572 942 | | 12/1993 |
| EP | 0 576 675 | | 1/1994 |
| EP | 0 612 520 | | 8/1994 |
| GB | 1085739 | | 10/1967 |
| GB | 2 203 143 A | | 10/1988 |
| WO | 92/16191 | | 10/1992 |
| WO | 92/17165 | | 10/1992 |
| WO | 92 17165 A | | 10/1992 |
| WO | 94/12160 | | 6/1994 |
| WO | 94 12160 A | | 6/1994 |
| WO | 97/02020 | | 1/1997 |
| WO | 97 02020 A | | 1/1997 |
| WO | 97/25979 | | 7/1997 |
| WO | 97 25979 A | | 7/1997 |

OTHER PUBLICATIONS

Bright et al, "Apoptosis: Programmed Cell Death In Health and Disease", *Bioscience Reports,* 14(2):67–81, 1994.

Kelloff et al, "Clinical Development Plan: Sulindac", *J. Cell Biochem Supp,* 20:240–251, 1994.

DiSario et al, "Sulindac Induces Regression and Prevents Progression of Sporadic Colorectal Adenomas", *Gastroenterology 112(Supp),* A555, Apr. 1997.

DuBois et al, "Nonsteroidal Anti–Inflamatory Drugs, Eicosanoids, and Colorectal Cancer Prevention", *Gastroenterology Clinics of North America,* 25(4):773–791, 1996.

Duggan et al, "The disposition of sulindac", *Clin Pharm Therapeutics,* 21(3):326–335, 1977.

Fenoglio et al, "Colorectal Adenomas and Cancer", *Cancer,* 50(11):2601–2608, 1982.

Gazzaniga et al, "Oral Colon–Specific Drug DeliverY Design Strategies", *S.T.P. Pharma Pratiques,* 4(5):336–343, 1994.

Giardiello et al, "Treatment of Colonic and Rectal Adenomas with Sulindac in Familial Adenomatous Polyposis", *New England J. Med.,* 328(18):1313–1316, 1993.

Gowen, G., "Complete Regression of Villous Adenomas of the Colon Using Piroxicam, and Nonsteroidal Anti–Inflamatory Drug", *Dis. Colon Rectum,* 39(1):101–102, 1996.

Hanif et al, Effects of Nonsteroidal Anti–inflamatory Drugs on Proloferation and on Induction of Aoptosis in Colon Cancer Cells by a Prostaglandin–Independent Pathway, *Biochem Pharm,* 52(2):237–245, 1996.

Hixson et al, "NSAID Effect on Sporadic Colon Polyps", *Am J Gastroenterology,* 88(10):1652–1656, 1993.

Kerr et al, "Apoptosis: A Basic Biological Phenomenon With Wide–Ranging Implications in Tissue Kinetics", *Br. J. Cancer,* 26(4):239–257, 1972.

Knutson et al, "Diagnostic and Therapeutic Colonoscopy", *Arch Surg,* 114(4):430–435, 1979.

Labayle et al, "Sulindac Causes Regression of Rectal Polyps in Familial Adenomatous Polyposis", *Gastroenterology,* 101(3):635–639, 1991.

Ladenheim et al, "Effect of Sulindac on Sporadic Colonic Polyps", Gastroenterology, 108(4):1083–1087, 1995.

Konishi et al, "Pathology of Colorectal Adenomas: a Colonscopic Survey", *J. Clin Path,* 35(8):830–841, 1982.

Lee, FD, "Importance of Apoptosis in the Histopathology of Drug Related Lesions in the Large Intestine", *J. Clin Path,* 46(2):118–122, 1993.

Lee, et al, "Selective Expression of Mitogen–Inducible Cyclooxygenase in Macrophages Stimulated with Lipopolysaccharide", *J. Biol. Chem,* 267(36):25934–25938, 1992.

Leserman et al, "Cell–Specific Drug Transfer from Liposomes Bearing Monoclonal Antibodies", *Nature,* 293(5829):226–228, 1981.

Levine et al, "Coating of Oral Beclomethesone Dipropionate Capsules with Cellulose Acetate Phthalate Enhances Delivery of Topically Active Antiinflammatory Drug to The terminal Ileum", Gastroenterology, 92(4):1037–1044, 1987.

Lockshin et al, "Programmed Cell Death–I. Cytology of Degeneration in the Intersegmental Muscles of the Pernyi Silkmoth", J. Insect Physiol., 11(2):123–133, 1965.

Logan et al, "Effect of Aspirin and Non–Steroidal Anti–Inflammatory Drugs on Colorectal Adenomas: Case–control study of Subjects Participating in the Nottingham Faecal Occult Blood Screening Programme", Br. Med. J., 307(6899):285–289, 1993.

Masferrer et al, "Endogenous Glucocorticoids Regulate an Inducible Cyclooxygenase Enzyme", Proc. Natl. Acad. Sci. USA, 89(9):3917–3921, 1992.

Maskens et al, "Histogenesis of Adenomatous Polyps in the Human Large Intestine" Gastroenterology, 77(6):1245–12511, 1979.

Meade et al, "Differential Inhibition of ProstagINDIN Endoperoxide Synthase (Cyclooxygenase) Isozymes by Aspirin and Other Non–Steroidal Anti–Inflammatory Drugs", J. Biol. Chem., 268(9):6610–6614, 1993.

Mitchell et al, "Selectivity of Nonsteroidal Anti inflammatory Drugs as Inhibitors of Constitutive and Inducible Cyclooxygenase", Proc. Natl. Acad. Sci. USA, 90(24):11693–11697. 1994.

Miyamoto et al, "Purification of Prostaglandin Endoperoxide Synthetase from Bovine Vesicular Gland Micxrosomes", J. Biol. Chem., 251(9):2629–2636, 1976.

Moorghen et al, "A Protective Effect of Sulindac Against Chemically–Induced Primary Colonic Tumours in Mice", J. Path., 156(4):341–347, 1988.

Morson, BC, "Evolution of Cancer of the Colon and Rectum", Cancer, 34(3):845–849, 1974.

Nakada et al, "Prednisolone Therapy for Intra–abdominal Desmoid Tumors in a Patient with Familial Adenomatous Polyposis", J. Gastroenterology, 32(2):255–259, 1997.

Neugut et al, "The Effect of Calcium and Vitamin Supplements on the Incidence and Recurrence of Colorectal Adenomatous Polyps", Cancer, 78(4):723–728, 1996.

Northway et al, "Piroxicam Decreases Postirradiation Colonic Neoplasia in the Rat", Cancer, 66(11):2300–2305, 1990.

Oshima et al, "Suppression of Intestinal Polyposis in $Apc^{\Delta 716}$ Knockout Mice by Inhibition of Cyclooxygenase 2 (COX–2)", Cell, 87(5):803–809, 1996.

Pasricha et al, "The Effects of Sulindac on Colorectal Proliferation and Apoptosis in Familial Adenomous Polyposis", Gastroenterology, 109(3):994–998, 1995.

Peleg et al, "Asperin and Nonsteroidal Anti–Inflammatory Drug Use and Risk of Subsequent Colorectal Cancer", Arch Internal Med, 154(4):394–399, 1994.

Piazza et al, "Antineoplastic Drug Sulindac Sulfide and Sulfone Inhibit Cell Growth by Inducing Apoptosis", Cancer Res, 55(14):3110–3116, 1995.

Piazza et al, "Selective Apoptosis of Neoplastic Cells Accompanies Polyp Regression in Familial Adebomatous Polyposis (FAP) Patients Treated with FGN–1 (Sulindac Sulfone): Evidence for a Cyclooxygenase Independent Mechanism", Gastroenterology, 12(4 Supp):A638, 1997.

Pritchard et al, "Apoptosis and Gastrointestinal Pharmacologyt", Pharacol. Ther., 72(2):149–169, 1996.

Rao et al, "Chemoprevention of Colon Carcinogenesis by Dietary Administration of Piroxicam, a Difluoromethylornithine, 16a–Fluoro–5–Androsten–17–One, and Ellagic Acid Individually and in Combination", Cancer Res, 51(17): 4528–4534, 1991$\alpha\alpha\beta\beta\beta\alpha$.

Reddy et al, "Dose–Related Inhibition of Colon Carcinogenesis by Dietary Piroxicam, a Nonsteroidal Anti–Inflammatory Drug, During Different Stages of rat Colon Tumor Development", Cancer Res, 47(20):5340–5346, 1987$\alpha$.

Reddy et al, "Chemoprevention of Colon Carcinogenesis by Concurrent Adminisration of Piroxicam, a Nonsteroidal Anti Inflammatory Drug with D, L– a– Difluromethylornith, and Onithine Decarboxylasde Inhibitor, in Diet" Cancer Res, 50(9):2562–2568, 1990 $\alpha\alpha\alpha\alpha\alpha\alpha\alpha$.

Reddy et al, "Inhibition of Colon Carcinogenesis by Prostglandin Synthesis Inhibitors and related Compounds", Carcinogenesis, 13(6):1019–1023, 1992.

Reddy et al, "Inhibitory Effect of Aspirinon Azoxymethane–Induced Colon Carcinogenesis in F344 Rats", Carcinogenesis, 114(8), 11493–11497, 11993 $\alpha\alpha$.

Rex et al, "Colonoscopic Miss Rates of Adenomas Determined by Back–To–Back Colonoscopies", Gastroenterology, 1112(111):24–28, 1997.

Rex et al, Relative Sensitivity of Colonoscopy and Barium Enema for Detection of Colorectal Cancer in Clinical Practice, Gastroenterology, 1112(1):117–23, 1997.

Riendeau et al, "Comparison of the Cyclooxygenase–11 Inhibitory Properties of Nonsteroidal antiinflammatory Drugs (NSAIDS) and Selective COX–2 Inhibitors, using Sensitive Microsomal and Platelet Assays", Can. J. Physiol. Pharmacol., 75(9):11088–1095, 1977.

Saffran et al, "A New Approach to the Oral Administration of Insulin and Other Peptide Drugs", Science, 233:1081–1084, 1986.

Rosenberg et al, "A Hypothesis: Nonsteroidal Anti–Inflammatory Drugs Reduce the Incidence of Large–Bowel Cancer", J. Natl. Cancer Institute, 83(5):355–358, 1991.

Savill et al "Apoptosis in Disease", Eur. J. Clin Invest, 24(1111):7115–723, 1994.

Appel et al, "Formulation and Optimization of a Modified Microporous Cellulose Acetate Latex Coating For Osmotic Pumps", Pharma Res, 9(12):1664–1667, 1992.

Ashford et al, "An In Vitro Investigation into the Suitability of pH–dependent polymers for Colonic Targeting", Intl J Pharma, 91:241–245, 1993.

Banaker, U.V., "Drug Delivery Systems of the 90's, Innovations in Controlled Release", Amer Pharm, NS27(2):39–48, 1987.

Cardenas et al, "Oral Immunization Using Live Attenuated Salmonella spp. As Cariers of Foreign Antigens", Clin Microbiol Rev, 5(3):328–342, 1992.

Cargill et al, "Controlled Gastric Emptying. 1. Effects of Physical Properties on Gastric Residence Times of Nondisintegrating Geometirc Shapes in Beagle Dogs", Pharma Res, 5(8):533–536, 1988.

Cargill et al, "Controlled Gastric Emptying. II. In Vitro Erosion and Gasric Residence Times of an Erodible Device in Beagle Dogs", Pharma Res, 6(6):506–509, 1989.

Chien, Y.W., "Potential Developments and New Approaches in Oral Controlled–Release Drug Delivery Systems", Drug Dev & Indust Pharm, 9(7):1291–1330, 1983.

Cornes, J.S, "Part II the Effect of Age on Peyer's Patches", GUT, 6(3):230–233, 1965.

Cummings, JH, "Progress Report Laxative Abuse", *GUT*, 15:758–766, 1974.

Desai et al, "A Floating Controlled–Release Drug Delivery System: In Vitro–In Vivo Evaluation", *Pharma Res*, 10(9):1321–1325, 1993.

Ermak et al, "Strategies for Oral Immunization and Induction of Gastric Immunity", *Proceed Intern Symp Control Rel Bioact Mater*, 22:196–197, 1995.

Fairbairn, JW, "The Active Constitiuents of the Vegetable Purgatives Containing Anthracene Derivatives", *J Pharmacy & Pharmacol*, 1(10):683–694, 1949.

Fara, JW, "Colonic Drug Absorption and Metabolism", *Third International Conference on Drug Absorption*, Edinburgh, 1988.

Forni et al, "Papaverine Hydrochloride Release from Ethyl Cellulose–Walled Microcapsules", *J Microencaps*, 5(2):139–146, 1988.

Godbillon et al, "Investigation of Drug Absorption from the Gastrointestinal Tract of Man III. Metroprolol in the Colon", *Br J Clin Pharmac*, 19:113s–118s, 1985.

Groning et al, "Oral Dosage Forms with Controlled Gastrointestinal Transit", *Drug Devel & Indust Pharmacy*, 10(4):527–539, 1984.

Hardcastle et al, The Action of Sennosides and Related Compounds on Human Colon and Rectum, *GUT*, 11:1038–1042, 1970.

Ingani et al, "Conception and In Vivo Investigation of Peroral Sustained Release Floating Dosage Forms with Enhanced Gastrointestinal Transit", *Intl J Pharmac*, 35:157–164, 1987.

Jimoh et al, "Pulsatile Release of FSH for Superovulation in Cattle", *Therigenology*, 43:645–656, 1955.

Kenyon et al, "The Effect of Food on the In Vivo Behavior of Enteric Coated Starch Capsules", *Int'l J Pharma*, 112:207–213, 1994.

Khan et al, "An Experiment to Determine the Active Therapeutic Moiety of Sulphasalazine", *The Lancet*, 2:892–895, 1977.

Klotz, U, "Clinical Pharmacokinetics of Sulphasalazine, its Metabolites and Other Prodrugs of 5–Aminosalicylic Acid", Clin Pharmacokinetics, 10:285–302, 1985.

Laakso et al, "Effects of Core Components on Indomethacin Release from Film–Coated Granules", *Int'l J Pharmac*, 67:79–88, 1991.

Levine et al, "Coating of Oral Beclomethasone Diproplonate Capsules with Cellulose Acetate Phthalate Enhances Delivery of Topically Active Antiinflammatory drugs to the Terminal Ileum", *Gastroenterology*, 92(4):1037–1044, 1987.

Lin etal, Calcium Alginate Beads as Core Carriers of 5–Aminosalicylic Acid, *Pharma Res*, 9(9):1128–1131, 1992.

Lindholm et al, "Controlled Release Tablets", *Pharm Ind*, 44(9):937–941, 1982.

Longer et al, "Fundamental Aspects of Bioadhesion", *Pharmacy Int'l*, 7(5):114–117.

Mardini, et al, "Effect of Polymer Coating On Faecal Recovery of Ingested 5–Aminosalicyclic Acid in Patients with Ulcerative Colitis", *GUT*, 28:1084–1089, 1987.

Mayersohn, M., "Principles of Drug Absorption", in: *Modern Pharmaceutics*, Banaker et al, eds., Marcel Dekker, Inc., New York, publ., 23–85, 1979.

McNiel et al, "Mucosal Surface pH of the Large Intestine of the Rat and of Normal and Inflamed Large Intestine in Man",*GUT*, 28:707–713, 1987.

Morimoto et al, "Enhancement of Rectal Absorption of Insulin in Polyacrylic Acid Aqueous Gel Bases Containing Long Chain Fatty Acid in Rats", *Int'l J Pharma*, 14:149–157, 1983.

Park et al, "Bioadhesive Polymers as Platforms for Oral–Controlled Drug Delivery: Method to Study Bioadhesion", *Int'l J Pharma*, 19:107–127, 1984.

Rasmussen et al, "5–Aminosalicylic Acid in a Slow–Release Preparation: Bioavailability, Plasma Level, and Excretion in Humans", *Gastroenterology*, 83(5):1062–1070, 1982.

Ritschel et al, "Biopharmazeutische Entwicklung und Beurteilung von Magensaftresistent Überzogenen Arzneiformen und Solchen mit Verlängerter, Wirksamkeit", In: Angewandte Bioparmazie, Wissenschaftliche Verlagsgesellschaft MBH, Stuttgart W. Germany, publ., 396–402, 1973.

Ritscel et al, "Drug Release Mechanism from Matrix and Barrier Coated Tablets Prepared with Acrylic Resin, With and Without Addition of Channeling Agents", *Pharm Ind.*, 49(7):734–739, 1987.

Ritchel et al, "Targeting in the Gastrointestinal Tract: New Approaches", *Meth Find Exp Clin Pharamacol*, 13(5):313–336, 1991.

Rubinstein, A. "Microbially Controlled Drug Delivery to the Colon", *Biopharma & Drug Disp*, 11:465–475, 1990.

Safwat SM, "Preparation and Characterization of Controlled–Release Tenoxicam Tabletss", *Eur. J Pharma Biopharm*, 40(5):321–326, 1994.

Sheth et al, "The Hydrodynamically Balanced System (HBS): A Novel Drug Delivery System for Oral Use", *Drug Dev & Indust. Pharmacy*, 10(2):313–339, 1984.

Smart et al, "An In–Vitro Investigation of Mucosa–Adhesive Materials for Use in Controlled Drug Delivery", *J Pharma Pharmacol*, 36:295–299, 1984.

Sun et al, "Fluidized–Bed Spray Coated Porous Hydrogel Beads for Sustained Release of Diclofenac Sodium", *J Controlled Rel*, 47:247–260, 1997.

Sutinen et al, "Water–Activated and pH–Controlled Release of Weak Bases from Silicone Reservoir Devices", *Int'l J Pharma*.

U. S. Pharmacopeia XXII, National Formulary XVII, p. 1579, 1990.

\* cited by examiner

Diclofenac Release from Tablets 229-99/A (5% CPV), Coated with Ethylcellulose/CaP (ratio 1:1).

Diclofenac Release from Tablets 229-93/B (hardness 11-13), Coated with Ethylcellulose/CaP (ratio 1:1).

Diclofenac Release from Tablets 229-93/A (hardness 5-6), Coated with Ethylcellulose/CaP (ratio 1:1).

Diclofenac Release from Tablets 263-129 (Granulated CaP+CPV+EC, Granulated Diclofenac+CPV+EC; 50% Emcocel; D=7mm), Coated with Ethocel 20/CaP (ratio 1:1).

Diclofenac Release from Tablets 263-123 (Granulated CaP+CPV+EC, Granulated Diclofenac+CPV+EC; 50% Emcocel; D=7mm), Coated with Ethocel 20/CaP (55% CaP).

Diclofenac Release from Tablets 229-76/A, Coated with Ethylcellulose/CaP (ratio 3:7). Form. 229-88.

IMMEDIATE RELEASE GASTROINTESTINAL DRUG DELIVERY SYSTEM

This application is a continuation of Ser. No. 09/163,202 filed Sep. 30, 1998 now abandoned.

FIELD OF THE INVENTION

The invention is directed to a drug delivery system for delivery of enterally-administered pharmaceuticals to specific locations along the gastrointestinal tract by immediate release (not sustained) of all or most of the drug at the specific location. The drug delivery system has the capability of complete loss of integrity in a very short space of time allowing delivery of virtually all of the drug contained therein at the location of disintegration. The features that allow this capability are a channel-forming coating allowing the controlled entry of liquid into a core and a core capable of absorbing liquid and swelling enough to cause breakage of a coating surrounding the core, the core disintegrating rapidly after the integrity of the coating is breached.

BACKGROUND OF THE INVENTION

Specific delivery of drugs to a selected target in the gastrointestinal tract is desired for the treatment of a wide variety of diseases and conditions. It is especially desirable to be able to deliver drugs so that they are targeted to, and absorbed at, specific regions of the gastrointestinal tract. Targeting drugs to specific regions along the gastrointestinal tract provides the ability to locally treat gastrointestinal diseases, thus avoiding systemic side effects of drugs or inconvenient and painful direct delivery of drugs. Such specific delivery also potentially increases the efficiency of the drug and enables a reduction of the minimum effective dose of the drug.

Delivery systems based on coatings exist in the art. Some systems have been reported to target particular parts of the body. For example, U.S. Pat. No. 5,593,697 describes a pharmaceutical implant containing a biologically active material, an excipient comprised of at least one water soluble material and at least one water insoluble material, and a polymer film coating adapted to rupture at a predetermined period of time after implantation. In one form, a bilayer film coating forms an impermeable barrier to the drug. An insoluble outer film controls the degree of access of physiological fluid to an inner film that is soluble at physiological pH. By varying the thickness of the outer film, access of the physiological fluid to the inner film, and thus the time before the failure of the inner film occurs, is said to be controlled. Failure of the inner film then permits a swellable excipient (disintegrant) to exert a force on the outer film which then ruptures releasing the core content. In another embodiment, a monolayer film is used. A film coating comprising a mixture of ethylcellulose and a copolymer of glycolic and lactic acid is used. Ethylcellulose is an insoluble polymer and thus when the PLGA polymer in the film hydrolyzes, the film becomes porous and allows release of the drug. The rate of hydrolysis of the PLGA depends on the ratio of lactic-to-glycolic acid in the polymer.

U.S. Pat. No. 4,252,786 describes a controlled release tablet for the administration of medicinal agents over a prolonged period of time. It involves the application of a film comprising a combination of hydrophobic and hydrophilic polymers to an insoluble swelling type delayed release matrix to modify the drug release rate. Initially when the film is intact, the release of the drug contained in the matrix is primarily controlled by diffusion of solvent and solute molecules through the film. As water or gastric fluid permeates through the film, the gummy complex forms in the core and the slight swelling of the complex causes the film to rupture or erode. The release rate is then controlled by the gummy complex. The application of a relatively water-insoluble water-permeable film primarily controls the drug release rate while the matrix gel is being generated and it is reported that this generates a smoother, gradual, more uniform, release rate during the period of about 8–12 hours, approaching a zero order release pattern.

U.S. Pat. Nos. 5,260,069 and 5,472,708 describe a dosage form for delivering drugs, and particularly drugs that cannot be released by diffusion through a porous coating, such as water insoluble drugs. Pellets are provided in a unit dosage form such as a capsule or tablet. The pellets are composed of a core containing the drug and swelling agent which expands in volume when exposed to water. The core is enclosed within a membrane or coating that is permeable to water. The membrane is composed of a water insoluble but permeable film forming polymer, a water soluble film forming polymer and a permeability reducing agent. Water diffuses through the coating and into the core. As water is taken up by the swelling agent the core expands, exerting force on the coating until it bursts, releasing the drug. The permeability reducing agent reduces the rate at which water reaches the swelling agent, thereby delaying release time. The water soluble polymer dissolves, weakening the coating so that it bursts sooner. By varying the proportions of the three coating ingredients and/or coating thickness, the release timing is reported to be effectively controlled.

U.S. Pat. No. 4,897,270 describes a pharmaceutical tablet comprising a tablet core and a film coat to mask the taste of the core. The core disintegrates immediately following rupture of the film coat. The film coat allows a permeation of moisture to the core which ruptures very rapidly upon contact with gastrointestinal fluid. Thus the core immediately disintegrates, allowing dispersion and dissolution of the drug.

U.S. Pat. No. 5,204,121 describes a drug release system in pellet form where the pellets consist of a core containing the active compound. The core is surrounded by a polymer-containing jacket and a undigestible lacquer layer that is permeable to water. The outer lacquer layer does not dissolve but carries water to the migration controlling jacket layer which then brings the liquid in contact with the drug containing core.

U.S. Pat. No. 4,891,223 describes compositions for the sustained release of a pharmaceutical, comprising a drug-containing core, a first coating containing a polymer swellable upon penetration of the surrounding media, and a second coating, enveloping the first coating, comprising a polymer that is water-soluble and that forms a semi-permeable barrier. The outer coating permits diffusion of the media, into the first coating and then diffusion of the dissolved drug into the surrounding media. The second coating must have requisite stretchability to prevent rupture of a second coating due the swelling of the first coating until a specific time in the release pattern.

U.S. Pat. No. 4,327,725 describes a variation of a basic osmotic device for drug release. The structure of the device is an active agent enclosed in a hydrogel layer that is enclosed in a semi-permeable membrane. The semi-permeable membrane allows diffusion of external fluid but does not allow diffusion of the solution of active agent to the surrounding environment. The hydrogel swells with absorption of external fluid and exerts pressure on the solution of active agent in the external fluid. The solution of the active agent in the external fluid is then delivered to the surrounding media through a single specially constructed passageway through the hydrogel layer and the membrane.

Delivery of Drugs in the Alimentary Canal

The targeting of drugs to desired locations in the alimentary canal can be complicated. Various factors must be taken into consideration for delivery to desirable areas of the alimentary canal. Each segment of the alimentary canal has distinct features which may hinder or favor permeation of drugs across the membrane. The following characteristics are to be taken into account:

1. Anatomic—Surface area, epithelium, presence of mucus cells, venous drainage, lymphatic drainage;
2. Physiologic features—absorption pathways, pH, motility and transit time, enzymes;
3. Biochemical features—endogenous secretion, pH, gut flora, enzymes;
4. Mechanical features—mucus and water coating layers and their turnover rate;
5. Immunological features—antigenic stimulation at the epithelial surface.

In the controlled release systems currently known in the art, drugs are released by diffusion and erosion throughout the gastrointestinal tract. Upon arrival at a target site a large portion of the drug may have already been released, leaving only a small portion of the drug for local delivery, or may pass through the site unreleased to a significant degree.

Delivery to the Stomach

Current techniques for targeting drugs to the stomach are based on the understanding that peroral sustained-release and controlled-release may be limited in duration by gastrointestinal transit time, which is closely related to the rate of gastric emptying. Approaches for the prolongation of gastric retention time, include incorporation of fatty acids to reduce physiological gastric emptying (Groning R., et al., *Drug Dev. Ind Pharm,* ID:527–39 (1984)) and the use of bioadhesive polymers. Such systems have been developed using polymers such as polycarbophyll, sodium carboxymethylcellulose, tragacanth gum, acrylates and methacrylates, modified celluloses and polysaccharide gums (Smart, J. D., et al., *J. Pharm. Pharmacol.* 36:295 (1984)).

Another system for targeting drugs to the stomach while avoiding gastric emptying is known as a hydrodynamically balanced system. This system is based on capsules or tablets with bulk density lower than gastric fluid. Thus, the dosage form stays buoyant in the stomach. These dosage forms are comprised of 20–75% of one or more hydrocolloids (e.g., hydroxyethylcellulose and hydroxypropylmethylcellulose (Sheth, P. R., *Drug Dev. Ind. Pharm.* 10:313–39 (1983); Chien, Y. W., *Drug Dev. Ind. Pharm* 9:1291–330 (1983); Desai, S. and Bolton, S., *Pharm. Res.* 10: 1321–5 (1993)).

Banakar (*Amer. Pharm.* 27: 39–48 (1987)) describes gastroinflatable delivery devices. The devices contain one or several inflatable chambers which are filled with gas at body temperature (e.g., a gasifying liquid or a gas-forming solid, such as bicarbonate or carbonate). The chambers are incorporated within a plastic matrix and encapsulated in gelatin. Dissolution of the gelatinous coating inflates the device and drug diffusion occurs.

Certain of the se devices include osmotic pressure compartments containing osmotically active salts. Dissolution of these salts by the gastric fluid pumps out the drug. Others are based upon a floating bilayer compressed matrix. (Ugani, H. M., et al., *Int. J. Pharmaceut.* 35:157–64 (1987). One of the layers is comprised of a hydrophilic polymer and a carbon dioxide-generating composition. The carbon dioxide maintains buoyancy and the other hydrophilic layer releases the drug from the matrix.

A further method for gastric drug targeting involves an intragastric retention shape, made of polyethylene or polyethylene blend (Cargill, R., et al., *Pharm. Res* 5:533–536 (1988); Cargill, R., et al., Pharm. Res. 5:506–509 (1989)).

Delivery to the Small Intestine

Delivery of drugs to sites beyond the stomach is especially desirable for drugs that are destroyed by the acid conditions or enzyme of the stomach, or for drugs that cause local irritation in the stomach. Mechanisms for targeting drugs to the stomach are applicable to the delivery of drugs to the upper small intestine. However, targeting to other areas of the small intestine involves several additional systems. The low stomach pH and presence of gastric enzymes have led forms in which the drug is provided with an enteric coating. This coating protects the gastric mucosa from drug irritation. Coating is done with a selectively insoluble substance, and protects drugs from inactivation by gastric enzymes and/or low pH.

The most common enteric coatings are methacrylic acid copolymers (Eudragits™), cellulose acetate phthalate, cellulose acetate succinate, and styrol maleic acid co-polymers (Ritschel, W. A., *Angewante Biopharmazie,* Stuttgart (1973), pp. 396–402; Agyilirah, G. A., et al., "Polymers for Enteric Coating Applications" in *Polymers for Controlled Drug Delivery,* Tarcha, P. J. ed., CRC Press, (1991) Boca Raton, pp. 39–66). The most significant drawback of enteric coating is the variability in gastric emptying time. This results in a large variance in blood drug levels.

Another method of drug targeting to the small intestine is drug absorption via the lymphatic system. Capillary and lymphatic vessels are permeable to lipid-soluble compounds and low molecular weight moieties (Magersohn, M., *Modern Pharmaceutics,* Marcel Dekker, New York (1979), pp. 23–85) (Ritschel, W. A., *Meth Find Ex. Clin. Pharmacol* 13(5):313–336 (1991)). Macromolecules, such as peptides, are absorbed into the lymphatics through Peyer's patches, which occur equally throughout all segments of the small intestine. Peyer's patches are most prevalent in young individuals and are characterized by age-related disappearance (Comes, J., *Gut* 6:230 (1965)).

At the Peyer's patches, the antigens are processed for presentation to regulatory T cells. The activated T cells migrate to the inflamed tissue, wherein suppressor cytokines neutralize T cells and any other inflammatory cells. This method is presently undergoing investigation (Ermak, T. H., et al., "Strategies for Oral Immunization and Induction of Gastric Immunity" in *Proceed. Intern. Symp. Control. Rel. Bioact. Mater.* 22: 334 (1995)). The major drawback of targeting drugs/peptides to Peyers patches in their reduced availability beyond middle age (Andreasen, *Acta Patrol. Microbiol. Scan.* 49 (suppl):81 (1943)). Therefore, they provide a target site for absorption until middle age. Targeting the Peyer's patches in a particular segment of the small intestine can be useful in limiting destructive side reactions. The lymphatic drainage of the small intestine provides an adsorptive window and has promoted design of delivery systems directed at this window (Norimoto et al., *Int. J. Pharm.* 14:149–157 (1983)).

Another approach for targeting drugs to the small intestine involves the use of intestinal sorption promoters. Studies have been carried out using long chain fatty acids, including linoleic acid, acylcarnitines, and palmitocamitine (Morimoto, K., et. al., *Int. J. Pharmaceut.* 14: 49–57 (1983); Fix, J. A., et. al., *Aires J. Physiol.* 14:G-332–40 (1986)).

Bioadhesives have also been used to prolong intestinal transit, as in buccal delivery systems. The adhesion to the intestinal mucosa takes place either by mechanical interlocking or other mechanisms (Longer, M. A., et. al., *Pharm. Int.* 7:114–7 (1986)).

Excipients for prolongation of GI transit time are also under development. Triethanolamine myristate has been shown to increase the gastrointestinal transit time and improve the absorption of riboflavine (Gronig, R. and Heun, G., *Drug Dev. Ind. Pharm.* 10:527–539 (1984); Palin, K. J., et al., *Int. J. Pharm.* 19:107–127 (1984)).

Most small intestinal-specific delivery systems are still experimental except for enteric-coated tablets. However, as discussed above, enteric coating cannot provide reproducible blood levels of drug. Thus, there is a need for a system that targets delivery of a desired agent to the small intestine.

Delivery to the Colon

Because of its location at the distal portion of the alimentary canal, the colon is particular difficult to access. Enteric coating has been used to bypass absorption in the stomach and deliver the drug to the small intestine. Delivery is based upon the pH differences between these two parts of the alimentary canal (Ritschel, W. A. *Angewndte Biopharmazio*, Stuttgart Wissensec. Verlag (1973), pp 396–402; Agyilirah, G. A. and Banker, G. S., "Polymers for Enteric Coating Applications" in *Polymers for Controlled Drug Delivery*, Tarcha, P. J., ed., CRC Press (1991) Boca Raton, pp.39–66). However, it has been demonstrated that the blood levels of enteric dosage forms are variable and erratic due to differences in gastric emptying rate. Also, enteric coatings do not allow for drug targeting to a particular part of the small intestine in a reproducible manner (Kenyon, C. J., et al., *Int. J. Pharm.* 112:207–213 (1994); Ashford, M., et al. *Int. J. Pharm.* 91:241–245 (1993)).

In current techniques for targeting drugs to the colon, solid formulations of the desired drug molecules are coated with a pH-resistant polymeric coating. Such formulations are similar to enteric coated formulations which may be used to deliver drugs to the distal ileum. Enteric coatings include bioerodible polymers such as shellac and cellulose acetate phthalate. (Levine et al., *Gastroenterology* 92:1037–1044 (1987)).

In contrast to the enteric coated formulations, however, the formulations for colonic delivery are designed to withstand both low and slightly basic pH values (around seven) for several hours. During this time, they are assumed to pass the stomach and the small intestine and reach the large intestine, where the coat disintegrates and the drug release process is initiated. In this way, drugs such as 5-amino salicylic acid (5-ASA), and some steroids have been delivered to the colon. The polymers used for this purpose are commonly acrylic acid derivatives or cellulose derivatives such as cellulose acetate phthalate, or ethyl cellulose (Rasmussen, S. N., et al., *Gastroenterology* 83:1062 (1982); Levine, D. S., et al., *Gastroenterology* 92:1037 (1987); Mardini H., et al., *Gut* 28:1084–1089 (1987)).

However, an important limitation of this technique is the uncertainty of the location and environment in which the coat starts to degrade. Depending upon the gastrointestinal motility pattern, which can vary widely in individual patients and in different disease states, degradation of the coating can occur deep in the colon, or within the small intestine.

The presence of short chain fatty acids, carbon dioxide, and other fermentation products, and residues of bile acids, often reduce the pH of the colon to approximately six (Stevens, C. E., *Amer. J. Clin. Nutr.* 31:S161 (1978); McNeil, N. I., et al., *Gut* 28:707 (1987)). This change in pH calls into question the reliance on higher colonic pH as a trigger.

The ability of the colonic flora to degrade substrates that are resistant to small bowel digestion has been studied as an alternative method for colonic delivery of drugs. This principle was utilized to deliver laxative products, mainly sennoside and related compounds (Fairbairn, J. W., *J. Pharm. Pharmacol.* 1:683 (1949); Hardcastle, J. D., et al., *Gut* 11:1038 (1970); Cummings, J. H., *Gut* 15:758 (1974)).

A drug traditionally used in the treatment of inflammatory bowel disease is sulfasalazine. Sulfasalazine is composed of the antibacterial sulfapyridine linked to the anti-inflammatory 5-ASA with an azo bond. The 5-ASA is responsible for the clinical effect (Khan, A. K., et al., *Lancet* 2:892 (1977)). The sulfasalazine is a prodrug which carries the active 5-ASA to the colon, where bacterial azo reduction releases the molecule with the desired therapeutic properties (Klotz, U., *Clin. Pharmacokin.* 10:285 (1985)). With the 5-ASA prodrugs (sulfasalazine, azodisalicylate and salicylazobenzoic acid), release of the parent drug is mediated by bacterial enzymes located at the target organ, rather than by enzymes of the target tissues. However, the azo compound is potentially toxic.

In U.S. Pat. No. 5,525,634, a delivery device is disclosed that contains a drug in combination with a matrix. The matrix contains a saccharide-containing polymer. The matrix-drug combination can be coated or uncoated. The polymer can be resistant to chemical and enzymatic degradation in the stomach and susceptible to enzymatic degradation in the colon by colonic bacteria. Whether the matrix is resistant or not to chemical and enzymatic degradation in the stomach, the mechanism of release of drug in the colon is by degradation of the matrix by colonic bacteria and the release of the drug embedded in the matrix as a result of the degradation of the matrix by colonic bacterial enzymes.

European patent 485840 (to Röhm GmbH), the application for which was published May 20, 1992, discloses a gastrointestinal delivery device containing, as a coating, a mixture of a polysaccharide and Eudragit™. However, this formulation does not allow control of the rate of liquid entry into the formulation. Therefore, control of the site of release of the drug cannot be achieved. Further, the polysaccharide is not provided in particulate form.

WO97/25979 describes a drug-delivery device that allows targeting to various parts of the gastrointestinal tract. A core containing a drug is coated with a hydrophobic polymer which contains hydrophilic, non-water-soluble particles embedded therein. These particles serve as channels for aqueous medium entering the core and for the release of drugs by diffusion through these channels. This delivery system can target various parts of the gastrointestinal tract and slowly release its drug load.

U.S. Pat. No. 4,627,850 (Deters et al.) discloses an osmotic capsule for the controlled rate delivery of a drug comprising outer and inner walls each formed of a different polymeric material, the inner wall defining a space containing the drug, with a passageway through the walls connecting the exterior of the outer wall with the interior of the inner wall.

U.S. Pat. No. 4,904,474 (Theeuwes et al.) discloses a colonic drug delivery device comprising means for delaying the delivery in the drug and in the small intestine and means for delivering the drug in the colon. This device comprises osmotic means for forcing the active pharmaceutical agent out from the compartment in which it is contained through an exit provided in said compartment, into the colon. The means for delaying delivery in the stomach or in the small intestine are pH-resistant coatings. The delay in delivery of the drug is time-based. The structure is so calculated that the contents of the inner drug-filled space are not forced out before the device has reached the preselected target region of the gastro-intestinal tract.

While there is evidence that certain proteins and peptides such as interleukin-II, interferon, colony-stimulating factor, tumor necrosis factor, and melanocyte-stimulating hormone may create new and effective therapies for diseases that are now poorly controlled, the acceptance of these proteins as drugs is currently limited by the methods of delivery. Colonic delivery may be a preferred route of administration for these and other new protein and peptide drugs. In addition, colonic delivery is also important for targeting drugs for the treatment of inflammatory bowel disease and ulcerative colitis. Treatment methods for other disease states of the colon could benefit from the immediate release of a drug in the colon. Severe constipation, whether idiopathic or caused by drugs (e.g. morphine, dopamine) or by disease states (e.g. Parkinson's, spinal chord injury, multiple sclerosis, diabetes mellitus) are often caused by dysfunction of colonic motility (Sarna, S. K., *Digest. Dis. & Sci.* 36:827–882 (1991); Sarna, S. K., *Digest. Dis. & Sci.* 36:998–1018 (1991)). These conditions are not satisfactorily treated by available laxative drugs.

Dysfunction of colon motility may be characterized by (i) inability of the colonic motor activity to propel fecal content into the caucad direction (colonic inertia or gastroparesis); and (ii) inability of the colonic motor activity to provide the propulsive force at the time of defecation (colonic pseudo-obstruction).

In most of the cases the dysfunction in the colonic motility originates in neurological disorders. Therapy in these cases should therefore be directed towards improving the transit of intraluminal contents, by modulating the neural control systems. Prokinetic agents are agents that enhance the transit of material through the GI tract. They affect the GI motility by action at specific cellular drug-receptor interactions, may interfere with the release of one or more mediators affecting GI motility, such as acetylcholine or dopamine, or may act directly on the smooth muscle. As a result, GI motility can be stimulated by dopamine antagonists, such as metoclopramide and domperidone, orby substances which enhance acetylcholine release, such as metoclopramide and cisapride, or by substances that directly bind to muscarinic receptors on the smooth muscle, such as bethanecol. These agents, however, were found to cause neuroendocrine side effects or to accelerate colonic transit with no consistent increase in the frequency of evacuations.

Reversible inhibitors of acetylcholinesterase, such as neostigmine and its salts, physostigmine and its salts and pyridostigmine bromide, have been shown to increase motility of the colon and to cause defecation and even diarrhea when administered intravenously or orally (Kreis, M. E. et al., *Gastroenterology* 114:S0128 (1998); Ponevc R. J., et al., *Gastroenterology* 114:G0140 (1998); Turegano-Fuentes, F., et al., *Dis. Colon Rectum* 40:1353–1357 (1997); Stephenson, B. M., et al., *The Lancet* 342:1181–1182 (1993); Keeler, J. R., et al.,*J. Am. Med. Assoc.* 266:693–695 (1991); Sadjapour, K., *J. Am. Med. Assoc.* 249:1148 (1983); Anderson, N. E., et al., *Neurology* 47:985–987 (1996); Battle, W. M., et al., *Gastroenterology* 79:1217–1221 (1980)). It is, however, not advantageous to administer these drugs systemically since they affect the smooth muscles of the entire body giving unacceptable side effects. Oral administration is also problematic because of erratic bioavailability and the possibility of the drugs causing side effects earlier in the gastrointestinal tract (Breyer-Pfaff, U., et al., *Clin. Pharmacol. Ther.* 3 7:495–501 (1985); Aquilonius, S. M., et al., *Eur. J. Clin. Pharmacol.* 18:423–428 (1980)).

There is also a need for delivery to the colon of drugs that are reported to be absorbable in the colon, such as, inter alia, steroids and xanthines. This would increase the efficiency and enable reduction of the required effective dose (Godbillon, J. et al., *British Journal of Clinical Pharmacology* 19:113S (1985); Antonin, K. et al., *British Journal of Clinical Pharmacology* 19:137S (1985); Fara, J. W., Third International Conference on Drug Absorption, Edinburgh (1988)). Propranolol, oxyprenolol, metropolol, timolol, and benazepril are known to be preferentially absorbed in the jejunum while cimetidine, flrosemide, hydrochlothiazide, and amoxicillin are known to be preferentially absorbed in the duodenum. For a review, see Rubinstein, A., *Biopharm. Drug Dispos.* 11:465–475 (1990).

The currently available enterally administered preparations of drugs designed for colonic delivery are not feasible for long-term use in humans, in part because of the potential toxicity of the azo compounds. There exists a need for an improved colonic delivery system that can be used with a wide variety of drugs and bioactive compounds. Especially, there exists a need for the delivery of drugs such as the above-mentioned drugs and other prokinetic drugs, to the colon and for their release therein in an immediate fashion to treat constipation. Such delivery should be advantageous in that it will allow delivery of the drug to the site of action thereby allowing the use of low doses and avoiding both the problems of bioavailability, of systemic side effects, and of local side effects in the upper gastrointestinal tract.

Thus, there is a need for an immediate delivery version of a targeted delivery system. Immediate delivery would provide an advantage where a high concentration of the drug is necessary for a relatively short period of time, whether for clinical reasons or to effect a concentration-driven gradient to enhance absorption.

SUMMARY OF THE INVENTION

The invention is directed to a delivery system or device for targeted delivery to one or more specific location in the alimentary canal. The delivery system or device contains a core and a coating. The core contains a drug in combination with a carrier material. This carrier material has the property of swelling upon contact with an aqueous medium such as that found in the alimentary canal. Thus, the core has the essential characteristics of the capability of absorbing a large amount of aqueous medium and of swelling considerably. However, the core has the further essential characteristic of disintegrating rapidly after the coating is broken. Thus, the coating used for the invention prevents drug release until the predetermined time when particulates in the coating have swollen enough to allow entry of aqueous medim into the core. The core swells and bursts the coating. The unveiled core then disintegrates, releasing its drug load.

Accordingly, in a first embodiment, the core provides the following components: a water insoluble polymer that swells considerably but does not form a strong gel (i.e., hydrogel), a disintegrant, and a hardness enhancer.

Useful water insoluble polymers include, but are not limited to, an insoluble metal salt of a polysaccharide such as calcium pectinate or calcium alginate, or a heavily cross-linked polysaccharide such as glutaraldehyde-cross-linked guar gum, pectin, alginic acid, or other vegetable gum. In preferred embodiments, calcium pectinate is the water insoluble polymer.

Useful disintegrants include, but are not limited to, Crospovidone. Other disintegrants are known in the art.

Useful hardness enhancers include, but are not limited to, microcrystalline cellulose.

In a preferred embodiment, the form of the core includes tablets and pellets, especially compressed tablets and matrix tablets.

The coating comprises a material that is not soluble, or minimally soluble, in aqueous solution, within which material a hydrophilic, non-water-soluble, particulate is embedded. The essential features of the coating are a relatively rigid hydrophobic polymer, embedded with particles of an insoluble hydrophilic polymer that allow entry of water in a controlled fashion. The particles preferably have the ability to swell. The coating serves to control the rate of liquid entry into the tablet. Factors that influence the rate of liquid intake are the weight percent of hydrophilic particles, the size of the particles, the swelling characteristics of the particles, and the degree of hydrophilicity. The core can also influence the rate of water intake for a given coating thickness. A relatively high concentration of water soluble salts in the core (relative to the outside of the tablet) causes a high osmotic gradient across the coating membrane, enhancing uptake of liquid.

This design allows the controlled introduction of water or aqueous medium, such as in the gastrointestinal tract, into the device. When the aqueous medium contacts the particulate matter, the particulate matter swells. The particles eventually form channels from the outer part of the device to the core containing the drug. The core imbibes fluid and then swells, breaks the coating, disintegrates, and all or most of the drug is released with a burst effect.

The core may be designed with varying rates of swellability, e.g., rapid swelling, moderately rapid, slow, etc.

Accordingly, the location of drug release is controlled by varying specific parameters such as the thickness of the outer coating, the amount of particulate embedded in the coating, the type of particulate embedded in the coating, the particle size distribution of the particulate embedded in the coating, the core carrier, the rate of core swelling, swellability of the particulate matter in the coating, hydrophilicity of the particulate matter in the coating, rate of core swelling, and salt concentration in the core.

Thus, the drug delivery system of the invention further provides a method for enterally administering a drug or other bioactive compound to a patient in need of such drug whenever it is necessary or desired that such drug be specifically provided locally in the gastrointestinal tract. In the invention, the drug is not released solely through channels created in the coating, but is released in a burst by a predetermined time at which the coating will be broken and tablet disintegration with simultaneous release of all or most of the drug occurs.

The invention is thus useful for local or targeted delivery of a drug where slow release is undesirable or where a high-peak concentration is necessary. It is also advantageous to improve the absorption of poorly absorbed drugs by providing a strong concentration gradient across the lumen at a point considered to be suitable, whether in the small intestine or in the colon, although in preferred embodiments the site of drug release is the colon.

The preferable areas of treatment include, but are not limited to, the ileum and the colon.

The drug delivery system further provides a method for delivering efficacious levels of one or more drugs designed for local treatment of diseases of particular areas of the alimentary tract. These diseases include, but are not limited to, Crohn's disease, colitis, irritable bowel syndrome (IBS), local spasmolytic action, ulceration of the mucosa, diarrhea, constipation, polyps, carcinomas, cysts, infectious disorders, and parasitic disorders. The drug delivery system further provides a method for oral immunization through either the Peyer's Patches or through the colon.

The drug delivery system further offers the opportunity for targeting the local delivery of agents for photodynamic therapy.

The drug delivery system also provides a method for the systemic delivery of efficacious levels of drugs through a targeted area of the alimentary canal. Drugs that are better absorbed, and/or show lesser side effects, in the distal parts of the alimentary canal can be directed to those sites. The delivery system allows delivery to the duodenum, jejunum, ileum, ascending colon, transverse colon, and descending colon as the site for systemic drug delivery.

The invention further provides methods for the preparation of the drug delivery system. The preferred method of preparation is by the preparation of a suspension of the hydrophilic, water-insoluble particulate in an alcoholic solution of a hydrophobic polymer. This suspension is spray coated onto the core tablet or capsule using conventional pan coating technology.

DETAILED DESCRIPTION OF THE PREFERRED EMBODIMENTS

Definitions

Figure 1:
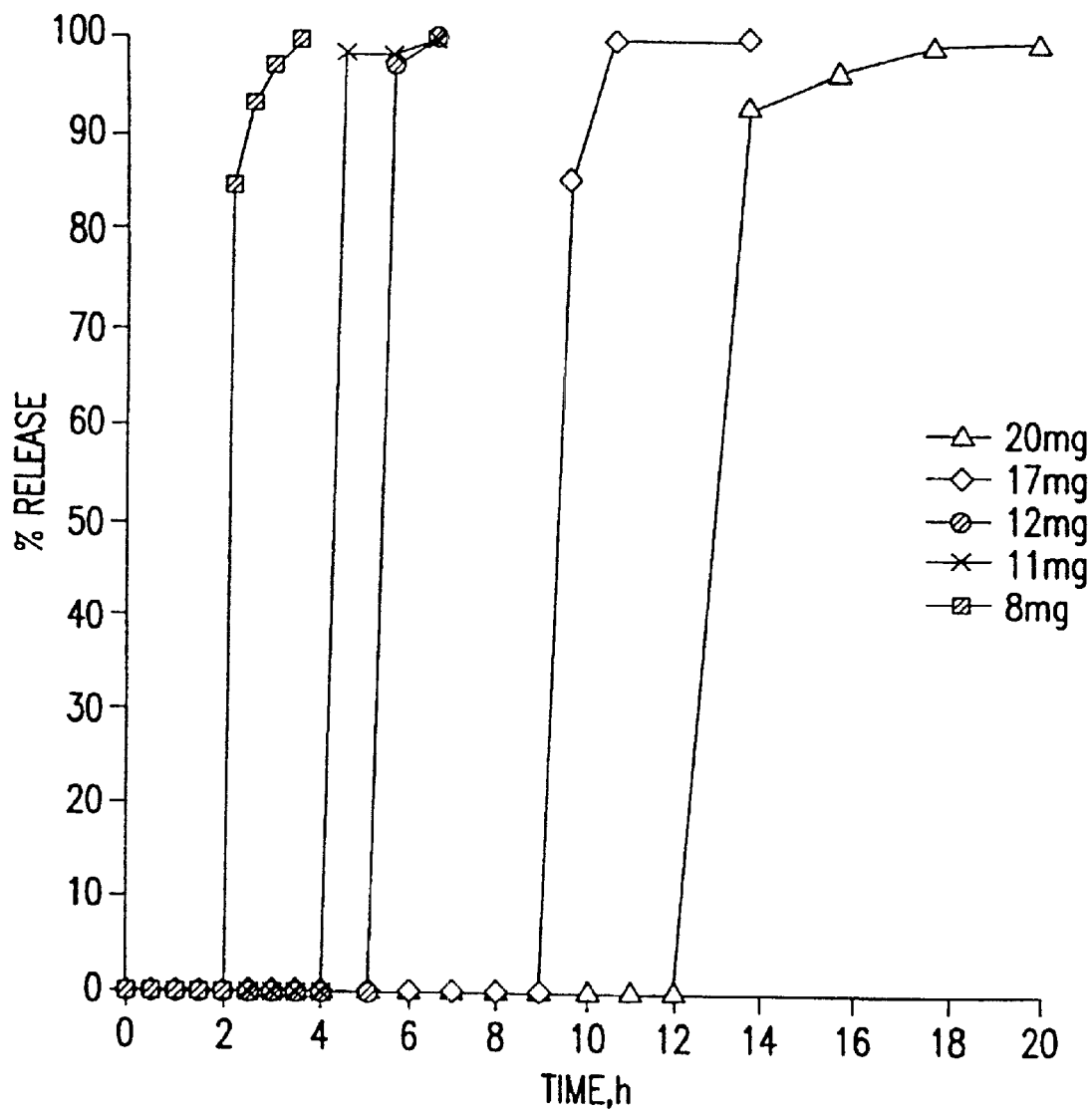
FIG. 1. Diclofenac release from tablets 229-76/A (10% CPV), coated with ethylcellulose/CaP (ratio 1:1).

In the description that follows, a number of terms used in pharmacology are extensively utilized in order to provide a clear and consistent understanding of the specification and claims, and the scope to be given such terms, the following definitions are provided. Where not specifically indicated, the terms used herein are used according to their normal and/or art-recognized meaning.

For example, the terms "colon," "large intestine," "small intestine," "stomach," "rectum" and "ileum" are all used according to their art-recognized meanings.

By the term "delivery device" or "delivery system" is intended a preparation that is contrived to deliver a desired agent, such as a drug. The preparation can be a combination of simple or complex formulations of chemicals, with or without excipients. The delivery can be controlled in that the site, time, rate of release and/or actual release and delivery of a desired agent may be preset by the composition of the formulation or preparation. Such control can occur by physical and/or chemical means. In the context of the invention, "delivery device" and "delivery system" are interchangeable.

By the term "drug" is intended any pharmaceutical or physiological agent, composition, bioactive compound, or combination thereof, useful in the diagnosis, cure, mitigation, treatment, or prevention of a disease, or for any other medical purpose. The term "drug" is intended to be interpreted broadly and is not limited in terms of chemical composition or biological activity.

By the term "core" is intended the central part of anything. With respect to the present invention, the term "core" in particular refers to that part of the drug delivery system that is surrounded by the particulate-containing coating and which contains the drug that is to be released from the delivery system.

By the term "particulate" is intended a composition composed of separate particles. In the context of the present invention, these separate particles are embedded in the coating material surrounding the core. It is the taking up of liquid by these particles that creates channels, pores, or networks that allow swelling of the core. When the insoluble polymer swells, the individual particles of that polymer swell but stay as individual particles. They do not coalesce into a single gel (i.e., coherent gel) that would prevent the tablet from disintegrating (i.e., behaving as a hydrogel).

In the context of the invention, "coat," "coating," "film," "layer," "covering," and the like are interchangeable.

By the term "water-insoluble" is intended not susceptible to being dissolved. Within the context of the present invention, the property of water-insolubility is important as follows. Both the hydrophobic film and the hydrophilic particulate are water-insoluble and insoluble in the fluids of the gastrointestinal tract. This property is important for the hydrophobic coat so as to prevent the premature dissolution of the coat and the subsequent non-controlled release of the drug. The property is furthermore important for the hydrophilic particulate so that the channels formed remain intact and continue to allow liquid flow to control the timed release of the drug. The dissolution of the particulate would result in empty channels that would cause undesirable accelerated water uptake and/or premature drug release.

Conversely, by the term "water-soluble" is intended susceptible of being dissolved. The term "hydrophobic" when applied to a film means, besides its normal definition, relatively non-permeable to water and to water-soluble compounds. The term "hydrophilic" when applied to a film, means, besides its normal definition, relatively permeable to water and to water-soluble compounds.

By the term "embedded" or "embed" is intended the firm fixation of a material in a medium. Within the context of the present invention, this term refers to particulate matter fixed in the coating medium.

The term "microcapsule", "microparticle", and "microsphere" are used in the art-recognized sense as spheroidal or partly spheroidal particles in the submicron to approximate 1000 micron range. The preferred ranges are from 1 to 200 microns, and especially from 2 to 100 microns.

By the term "channel." is intended that through which anything flows. In the context of the present invention, it is the connection formed from the uptake of water and swelling of the particulate matter in the coating such that there is continuous contact among the swollen particulate matter to form conduits through which the aqueous medium outside of the delivery system or device is ultimately brought into contact with the core material in the device.

By the term "administer" is intended to mean introducing the delivery system or device of the present invention into a subject. When administration is for the purpose of treatment, administration may be for either prophylactic or therapeutic purposes. When provided prophylactically, the substance is provided in advance of any symptom. The prophylactic administration of the substance serves to prevent or attenuate any subsequent symptom. When provided therapeutically, the substance is provided at (or shortly after) the onset of a symptom. The therapeutic administration of this substance serves to attenuate any actual symptom.

By the term "animal" is intended any living creature that contains cells in which the devices of the present invention can be effective. Foremost among such animals are humans; however, the invention is not intended to be so limiting, it being within the contemplation of the present invention to apply the compositions of the invention to any and all animals which may experience the benefits of the invention. Thus, the delivery system and methods of the invention are not limited to administration to humans and are especially useful for veterinary administration of drugs to any animal, including (but not limited to) pets such as dogs, cats, horses, fish and birds, zoo animals, wild animal control and treatment, and agriculturally important animals of the food and dairy industry such as cattle, milk cows, swine and poultry.

The invention is directed to a delivery system or delivery device that contains a water-insoluble or relatively water-insoluble coating around a drug-containing swellable core. The coating consists of a hydrophobic polymer that resists water entry into the tablet with hydrophilic, nonsoluble particles, that are capable of swelling (but do not necessarily need to) through which aqueous solution enters the tablet in a controlled manner. The coating serves to control the rate of liquid entry into the tablet. The design is such that the coating determines the rate of water uptake while the swelling of the core, which depends on the rate of water uptake and on the swelling properties of the core itself, determines the time of breach of the coating.

The properties of the core further give it the characteristic that it disintegrates after breach of the coating, giving a burst of drug release at a predetermined site in a gastrointestinal tract. The drug may be embedded in the core material or otherwise associated with the core material, for example by dry admixture, or wet granulation. The core can be in the form of a matrix tablet or a capsule containing the drug. The core can be in the form of pellets of the pure drug. Alternatively, the core can contain pellets of the drug layered onto a separate core material. Alternatively, the core can contain microcapsules that contain the drug material. More than one of these forms can be present and more than one drug can be delivered in the same delivery system. In all of these forms, release of drug from the core is effective. The core has the essential characteristics of being capable of absorbing sufficient liquid so that it swells considerably, and disintegrates rapidly after the coating is breached. By "swelling considerably" is intended that sufficient swelling occurs so as to bring about and result in a pressure that initiates and/or otherwise facilitates disintegration. By "disintegrating rapidly" is intended that the disintegration occurs essentially in a burst, the burst being sufficient to release efficacious amounts of the drug from the delivery device or system.

The essential components of the core are (1) an insoluble polymer that is capable of swelling considerably but that does not form a strong gel, (2) a disintegrant, and (3) a hardness enhancer. An example of a useful water insoluble polymer includes, but is not limited to, a water insoluble metal salt of a polysaccharide. In a preferred embodiment, the polymer is calcium pectinate or calcium alginate. In a highly preferred embodiment, calcium pectinate is most preferred. When calcium pectinate is used, it is preferably present in the core at a range of around of 20–70% (weight/weight); more preferably, 30–60%.

Another example of a useful water insoluble polymer is a heavily cross-linked polysaccharide. Preferred embodiments of such polysaccharides include glutaraldehyde cross-linked guar gum, pectin, and alginic acid. Other useful polymers include other cross-linked vegetable gums.

If a polymer is cross-linked, the cross-linking should be such that the polymer swells considerably but does not form a coherent gel. The proper degree of cross-linking (i.e., "heavy" within the context of the invention) means that a large percent of the monomer units are cross-linked, or alternatively, that there are many cross-links per polymer chain. The absolute degree of cross-linking is flexible, and is based on the desired result as explained above. Thus, cross-linking can be correlated with hydrogel formation by assays known in the art.

Disintegrants include, but are not limited to, Crospovidone and microcrystalline starch, although any suitable disintegrant is relevant. These would be known to the ordinary skilled artisan. A reference listing disintegrants and other types of dosage components can be found, for example, in *Pharmaceutical Dosage Forms: Tablets,* Vol. 1, Herbert A. Lieberman, et al., eds., Second Edition, Marcell Dekker Inc., New York, N.Y. (1984). In a highly-preferred embodiment, Crospovidone is the preferred agent. The Crospovidone is preferably present in the core at a range of about 5–12% (weight/weight) and most preferably around 10%.

The core also includes a hardness enhancer. Useful hardness enhancers include, but are not limited to, microcrystalline cellulose (Emcocel™), starch, polyvinylpyrrolidone, low molecular weight hydroxypropylcellulose, and low molecular weight hydroxypropylmethylcellulose. In a preferred embodiment, microcrystalline cellulose (MCC) is the hardness enhancer. MCC is preferably present in the core at a range of about 20–50% (weight/weight), and most preferably 30–40%.

The core optionally contains lubricants, such as magnesium stearate or talc, glidants, such as fumed silica, binders for granulates, such as ethylcellulose, polyvinylpyrrolidone, and pectin, with ethylcellulose (NF-7) as the binder. However, other binders are known in the art (*Pharmaceutical Dosage Forms: Tablets,* Vol. 1, Herbert A. Lieberman, et al., eds., Second Edition, Marcell Dekker Inc., New York, N.Y. (1984)). Thus, the core material can include normal pharmaceutical additives and excipients. (See *Handbook of Pharmaceutical Excipients,* 2nd ed., Wade, A. and Weller, P. J., eds., American Pharmaceutical Association (1994)).

Combinations of materials are also useful for the core. For example, additional useful core materials include, but are not limited to, combinations of calcium pectinate, microcrystalline starch, starch, polyvinylpyrrolidone, microcrystalline cellulose, calcium phosphate, and cross-linked guar gum. In preferred embodiments, the core material includes a combination of calcium pectinate; microcrystalline starch, starch, microcrystalline cellulose, and calcium phosphate.

In a preferred embodiment, the core material includes calcium pectinate, Crosprovidone, microcrystalline cellulose, starch, or microcrystalline starch or any combination thereof. Alternate core materials include, but are not limited to, carboxymethylcellulose, calcium alginate, cross-linked guar gum, cross-linked polysaccharide, cross-linked vegetable gum, cross-linked hydrophilic polymer, alginic acid, sodium alginate, carrageenan, or any other standard tablet excipient known to those in the art. (See *Handbook of Pharmaceutical Excipients,* 2nd ed., Wade, A. and Weller, P. J., eds., American Pharmaceutical Association (1994)).

The coating is a mixture of a water-insoluble hydrophilic particulate material embedded and dispersed in a non-water-soluble material. The coating need not be completely non-water-soluble. The important parameter is that it allows the slow introduction of water or other aqueous fluid, such as that found in the gastrointestinal tract. When the liquid reaches the embedded hydrophilic particles, the particles imbibe liquid. The particles eventually form channels from the outer part of the device to the core containing the drug. Thus, aqueous medium enters through the channels in a controlled manner, causing swelling of the core. The coating is breached at a predetermined time, and the core then disintegrates. The core swells to the point at which the integrity of the coating is breached and all or most of drug is released in a burst (a short period) at the breach site. The coating is designed to be breached at a predetermined time so that the core disintegrates and all or most of the drug is released at the desired breach site.

The essential features of the coating are that it contain (1) a relatively rigid hydrophobic polymer, and (2) insoluble hydrophilic polymer particles, that preferably swell in liquid, and that allow the entry of liquid into the core in a controlled fashion by means of channels formed thereby. The polymer should be rigid enough so that when it is cast as a film, including the non-soluble hydrophilic particle, the "toughness" parameter—which is the area under the stress-strain curve in which the polymer does not tear (units are energy/area)—will give values of 0.009–0.21 MPa.

Useful relatively rigid hydrophobic polymer includes, but are not limited to, ethylcellulose, Eudragit RL™, Eudragit RS™, shellac and zein. Ethylcellulose is the preferred polymer. Ethylcellulose NE-20 is a highly preferred polymer. Eudragit RL™ is a dimethylaminoethylacrylate/ethylmethacrylate copolymer, a copolymer based on acrylic and methacrylic acid esters with a low content of quaternary ammonium groups. The molar ratio of the ammonium groups to the remaining neutral. (meth)acrylic acid esters is about 1:20. This polymer corresponds to USP/NF "Ammonio Methacrylate Coplymer Type A."

Eudragit RS™ is an ethylmethacrylate/chlorotrimethylammoniumethyl methacrylate copolymer, a copolymer based on acrylic and methacrylic acid esters with a low content of quaternary ammonium groups. The molar ratio of the ammonium groups to the remaining neutral (meth)acrylic acid esters is 1:40. The is polymer corresponds to USP/NF "Ammonio Methacrylate Copolymer Type B."

Eudragit L™ is a methacrylic acid/methylmethacrylate or ethylacrylate copolymer, an anionic copolymer based on methacrylic acid and methylmethacrylate or on methacrylic acid and ethylacrylate. The ratio of free carboxyl groups to the ester groups is approximately 1:1. This polymer corresponds to USP/NF "Methacrylic Acid Copolymer Type A and Type C."

The insoluble hydrophilic particles in the coating are preferably particles that will swell. Examples of useful substances for such particles includes, but is not limited to, polysaccharides. Such polysaccharides include, but are not limited to particles of calcium pectinate, calcium alginate, calcium xanthate, any metal salt of a polysaccharide containing an acid group where the salt renders the polysaccharide insoluble in water, microcrystalline starch, insoluble starch, any water insoluble polysaccharide (e.g., cellulose or microcrystalline cellulose), any polysaccharide rendered insoluble by interacting with a poly-cation or poly-anion, and any covalently crosslinked polysaccharide where said crosslinking renders the polysaccharide insoluble in water. Such crosslinking agents include, but are not limited to, glutaraldehyde, formaldehyde, epichlorohydrin, diacid chlorides, diisocyananates, diacid anhydrides, and diamines. In a highly-preferred embodiment, the particulate matter is, or contains, calcium pectinate.

The coating material may optionally contain a plasticizer to improve its properties as is known in the art.

The coating that is next to the core and surrounds the core may be optionally coated with its own, outer coating, especially an enteric coating, as known in the art. This is especially useful if the core's coating material or the particulate embedded therein is adversely affected by the acid conditions of the stomach. Additional outer coatings include, but are not limited to, coatings to ease swallowing or mask taste.

In preferred embodiments, the coating material that is next to the core and into which the particles are embedded contains calcium pectinate (as the hydrophilic non-soluble particles) and Eudragit RL™ or Eudragit RS™ (as the hydrophobic film), Crospovidone and Eudragit RL™ or Eudragit RS™, or calcium pectinate and ethylcellulose. In the most preferred embodiment, the coating material comprises calcium pectinate and ethylcellulose, most preferably ethylcellulose NE-20.

The water insoluble carrier may or may not include a plasticizer according to the normal properties of a film as known to those skilled in the art.

In alternate embodiments, the coating includes, but is not limited to, any combination of a water-insoluble polysaccharide, water-insoluble crosslinked polysaccharide, a water-insoluble polysaccharide metal salt, a water-insoluble crosslinked protein or peptide, a water-insoluble crosslinked hydrophilic polymer in a dried powder form as the particulate and any hydrophobic polymer coating known in the art as the water-insoluble carrier. Specific examples of useful particulate material include, but are not limited to, insoluble starch, microcrystalline starch, microcrystalline cellulose, chitosan, calcium or zinc alginate, calcium xanthate, guar gum borax complex, glutaraldehyde- or formaldehyde-crosslinked guar gum, glutaraldehyde- or formaldehyde-crosslinked dextran, epichlorohydrin-crosslinked dextran, glutaraldehyde- or formaldehyde-crosslinked soluble starch, glutaraldehyde- or formaldehyde-crosslinked hydrolyzed gelatin, glutaraldehyde- or formaldehyde-crosslinked gelatin, glutaraldehyde- or formaldehyde-crosslinked collagen, any insoluble complex of a polysaccharide and a protein or peptide, glutaraldehyde- or formaldehyde-crosslinked hydroxypropylcellulose, glutaraldehyde- or formaldehyde-crosslinked hydroxyethylcellulose, glutaraldehyde- or formaldehyde-crosslinked hydroxypropylmethylcellulose, or any of the carbomers (crosslinked acrylic acid polymers). Specific examples of the water-insoluble carrier include, but are not limited to, Eudragit RL™, Eudragit RS™, ethylcellulose, shellac, and zein.

In a preferred embodiment of the invention, the delivery system or device is a tablet that contains a core material which is a disintegrating tablet. The tablet is made with standard granulation and tableting techniques and is coated using pan coat technology. Instead of a solution, a suspension of the particulate material in a solution or fine suspension of the polymeric coating material is sprayed on the tablets. The suspension is stirred to keep it relatively homogeneous. Warm or cold air is flowed over the tablets to allow for the film to form and the tablets to dry. Suitable solvents for such polymeric solutions or suspensions are the typical solvents known to those in the art for spray coating tablets and include, but are not limited to, water, ethanol, acetone and isopropanol. Ethanol is the preferred solvent.

It should be recognized however that any swellable material, is potentially useful as the core material. The functional requirement is simply that upon contact with aqueous matter in the gastrointestinal tract and following contact with channels formed by the particulate matter that has absorbed water, the core swells enough to break the coating and disintegrates enough to allow all or most of the drug present in the core to be released in a burst. Any material can be used as empirically determined to cause the necessary amount of swelling.

It should also be recognized that any material can form the embedded particulate. The functional requirement is that the material absorb aqueous matter from the gastrointestinal tract thereafter forming channels or networks whereby aqueous matter can flow into the core and allow it to swell.

Drug release is controlled by varying the following parameters: (1) size of the particulate matter; (2) thickness of the coating; (3) type of material forming the particulate matter; (4) ratio of particulate matter; (5) water-insoluble film forming material; (6) swelling of the particulate matter; (7) intrinsic hydrophilicity of particulate matter; (8) rate of swelling of the core; and (9) salt concentration in the core.

The core diameter can range from 1 mm to 15 mm, and is preferably 6–9 mm. The coating level can range from 2 to 50 mg/cm$^2$, and is preferably from 4 to 20 mg/cm$^2$. The percent of particulate matter in the coating can range from 1 to 95%, and is preferably 50–70%. The particle size of the particulate matter can range from 0.1 micron to 500 microns, and is preferably from 1 to 150 microns.

In particularly preferred embodiments, the delivery system or device is a 9 mm tablet of a drug (e.g., sodium salicylate or sodium diclofenac), a polymer that swells (e.g., calcium pectinate), an agent that causes tablet disintegration (e.g., Crospovidone) and a hardness enhancer (e.g., microcrystalline cellulose) coated with a suspension of one part calcium pectinate and one part ethylcellulose in 20–30 parts ethanol. The best results are obtained with calcium pectinate of particle size <149$\mu$ and a film coating of 13 mg/cm$^2$. This embodiment allows for delivery of a soluble drug to the colon since it affords an approximate four hour delay in drug release under in vitro conditions of USP Intestinal TS (*U.S. Pharmacopeia XXII, National Formulary XVII,* page 1789 (1990)) when using dissolution apparatus 2 (*U.S. Pharmacopeia XXII, National Formulary XVII,* page 1579 (1990)).

The preferred embodiment is coated with Eudragit L™ as an enteric coat to protect the calcium pectinate from the effects of the acid pH of the stomach. The enteric coat dissolves in the upper part of the small intestine. The particulate calcium pectinate starts to slowly swell as intestinal fluid enters the coating. After about four hours, channels have formed, the core has swollen and the drug is released in a burst upon tablet disintegration. A thinner coat will reduce the delay in drug release and allow delivery of the drug to the distal portion of the small intestine.

Thus, the drug delivery system serves as a means to target enterally administered drugs to various regions of the gastrointestinal tract. Accordingly, a subject in need of treatment with the desired agent, may conveniently obtain such treatment by orally ingesting the compositions of the invention.

Examples of agents that are useful for colonic delivery include nonsteroidal anti-inflammatory drugs (NSAID) such as sulindac, diclofenac, flurbiprofen, indomethacin, and aspirin; steroid drugs such as dexamethasone, budesonide, beclomethasone, flucticasone, tioxocortol, and hydrocortisone; contraceptives or steroidal hormones such as estrogen, estradiol and testosterone; immunosuppressants such as cyclosporin; bronchodialators such as theophylline and salbutamnol; anti-anginals and anti-hypertensives such as isosorbide dinitrate, isosorbide mononitrate, nitroglycerine, nifedipine, oxyprenolol, diltiazem, captopril, atenolol, benazepril, metoprolol, and vasopril; anti-spasmodic agents such as cimetropium bromide; anti-colitis agents such as 5-aminosalicylic acid; anti-arrhythmia agents such as quinidine, verapamil, procainamide, and lidocaine; anti-neoplastic agents such as methotrexate, tamoxifen, cyclophosphamide, mercaptopurine, and etoposide; protein or peptide drugs such as insulin, human growth hormone, interleukin-II, interferon, calcitonin, leuprolide, tumor necrosis factor, bone growth factor, melanocyte-stimulating hormone, captopril, somatostatin, somatostatin octapeptide analog, cyclosporin, renin inhibitor, superoxide dismutase, other hormones and vaccines; proteins or peptides containing antigens of tissues under autoimmune attack for absorption via Peyers patches (Cardenas, L. and Clements, J. D., *Clin. Microbiol. Rev.* 5/3: 328–342 (1992), anticoagulants such as heparin or short chain heparin, anti-migraine drugs such as ergotomine; glibenclamide; 5-hydroxytryptamine type$_{1A}$ receptor agonist gepiron; 5HT$_3$ antagonist ondasteron; metkephamid; menthol; antibiotics such as neomycin, β-lactams such as ampicillin and amoxicillin, cephalosporins such as cephalexin and cloxacillin, and macrolides such as erythromycin; PGE$_1$ analogues for protecting the gastroduodenal mucosa from NSAID injury, such as misoprostol; prokinetic drugs such as metoclopramide and cisapride; cholinergic agonists such as bethanecol, carbachol, methacholine and pilocarpine; dopamine antagonists such as metoclopramide and domperidone; and reversible inhibitors of acetylcholinesterase, such as neostigmine and its salts, physostigmine and its salts, and pyridostigmine bromide. Protein drugs, such as LH-RH and insulin, may survive longer and be absorbed better from the colon than from the small intestine. Other drugs have been shown to possess colonic absorption, such as diclofenac, quinidine, theophylline, isosorbide dinitrate, nifedipine, oxprenolol, metoprolol, glibenclamide, 5-hydroxytryptamine type$_{IA}$ receptor agonist gepiron, 5HT$_3$ antagonist ondasteron, metkephamid, menthol, benazepril (ACE inhibitor).

Examples of drugs that are useful for treating various other regions of the alimentary canal are as follows: Gastro Esophagal Reflux Disease—H2 receptor antagonists (e.g., Tagamet, Zantac), proton pump inhibitors (e.g., Omeprazole); *Candida esophagitis*—nystatin or clotrimazole; Duodenal Ulcer—H2 receptor agonists, prostaglandins (e.g., Cytotec, Prostin), proton pump inhibitors—(e.g., Prilosec, Omeprazole, Sucralfate); Pathological Hypersecretory Conditions, Zollinger-Ellison Syndrome—H2 receptor agonists; Gastritis—H2 receptor agonists, PGE$_1$, analogs for protecting the gastroduodenal mucosa from NSAID injury such as misoprostol, GHR-IH drugs for treating pancreatitis, such as somatostatin, and anti-spasmodic drugs for treating local spasmolytic action such as cimetropium bromide.

The therapeutic benefits of the delivery system depend upon its ability to delivery efficacious levels of drugs to a specific site in the gastrointestinal tract. This allows the local treatment of diseases including, but not limited to, ulcerative colitis, Crohn's disease, colon carcinoma, esophagitis, *Candida esophagitis,* duodenal ulcers, gastric ulcers, Zollinger-Ellison Syndrome (gastrinoma), gastritis, chronic constipation, diarrhea, pancreatitis, local spasms, local infections, parasites, and other changes within the gastrointestinal tract due to effects of systemic disorders (e.g., vascular inflammatory, infectious and neoplastic conditions).

Direct delivery of drugs to these regions enhances the amount of drug absorbed in this region and the amount of drug to which the cells in the region are directly exposed. Direct delivery or targeting of drugs also decreases the systemic distribution of drugs and thereby reduces undesirable and potentially harmful side effects.

High concentrations of a drug obtained by an immediate release of the drug in a predetermined section of the gastrointestinal tract may enhance absorption of poorly-absorbable drugs by means of an enhanced concentration gradient.

The delivery system or delivery device is also useful for diagnostic purposes, such as site-specific delivery of x-ray contrast agents (e.g., barium sulfate, Diatrizoate Sodium, other iodine containing contrast agents) ultrasound contrast agents (e.g., air-containing microspheres), contrast or enhancement agents for magnetic resonance imaging, tomography, or positron emission agents. The delivery system and delivery device are further useful for the delivery of monoclonal antibody markers for tumors.

Specific embodiments of prepared formulations of the compositions of the invention, include, for example, matrix-drug tablets, especially tablets prepared by compression; matrix-drug pellets, either free or packed in geladine capsules, or any other means allowing oral administration; matrix-drug nanoparticles, either free or packed in gelatine capsules or any other means allowing oral administration; and multi-layered tablets, coated capsules, coated microcapsules, coated pellets or micropellets, coated pellets or micropellets in a capsule, coated pellets or micropellets in a coated capsule, coated pellets, micropellets or microcapsules pressed into a tablet and coated pellets, micropellets or microcapsules pressed into a tablet and further coated. All of the techniques for preparation of such formulations are well known in the art.

The amount of drug can vary as desired for efficacious delivery of the desired drug and in consideration of the patient's age, sex, physical condition, disease, and other medical criteria. In addition, the amount of drug delivered by the system of the invention will depend upon the relative efficacy of the drug. The amount of specific drug necessary for efficacious results in the delivery system and methods of the invention may be determined according to techniques known in the art. For example, recommended dosages such as known in the art (or example, see the *Physicians' Desk Reference,* (E. R. Barnhart, publisher), *The Merck Index,*

Merck & Co., New Jersey, and *The Pharmacological Basis of Therapeutics,* A. G. Goodman et al., eds., Pergamon Press, New York), provide a basis upon which to estimate the amount of a drug which has been previously been required to provide an efficacious level of activity.

Examples of drugs whose efficacious amounts for use in the delivery system of the invention may be determined in this manner include anti-inflammatory agents, including non-steroidal and steroidal anti-inflammatory agents, such as sulindac, indomethacin, diclofenac, flurbiprofen, aspirin, dexamethasone, budesonide, beclomethasone, flucticasone, tioxocortal, and hydrocortisone; immunosuppressants, such as cyclosporin; bronchodialators, such as salbutamol and theophylline; anti-anginals and anti-hypertensives, such as diltiazem, captopril, nifedipine, isosorbide dinitrate, oxyprenolol; anti-spasmodics, such as cimetropium bromide; anti-neoplastic agents, including methotrexate, tamoxifen, cyclophosphamide, mercaptopurine etoposide; anti-colitis drugs, such as 5-aminosalicylic; and anti-arrhythmia agents, such as quinidine, verapamil, procainamide and lidocaine; protein or peptide drugs, such as insulin, human growth hormone, interleukin-II, interferon, calcitonin, leuprolide, tumor necrosis factor, bone growth factor, melanocyte-stimulating hormone, captopril, somatostatin, somatostatin octapeptide analog, cyclosporin, renin inhibitor, superoxide dismutase; other hormones; vaccines; anti-coagulants, such as heparin or short chain heparin; anti-migraine drugs, such as ergotamine; prokinetic drugs such as metoclopramide and cisapride; cholinergic agonists such as bethanecol, carbachol, methacholine and pilocarpine; dopamine antagonists such as metoclopramide and domperidone; and reversible inhibitors of acetylcholinesterase, such as neostigmine and its salts, physostigmine and its salts, and pyridostigmine bromide.

Tablets and capsules may be prepared and tested by techniques well known in the art, for example, as described in *Remington's Pharmaceutical Sciences,* Mack Publishing Company, and especially in chapter 89, the pharmaceutical preparation and manufacture of "Tablets, Capsules and Pills." In all embodiments, if desired, more than one drug may be supplied to the patient in the same matrix.

In the tablet embodiments, for example, the compositions of the invention may provide a wide range of drug amounts, for example, the amount of drug can vary from about 0.01–95% by weight.

In another embodiment, a compressed tablet is formulated to contain efficacious levels of the desired drug(s) or pharmaceutical compound(s) as in the tablet embodiment, and an amount of the components of the invention that would allow disintegration of the tablet and release of the drug(s) following exposure of the tablet to one or more microorganisms present in the colon. Other suitable embodiments will be known to those of skill in the art.

The following examples further describe the materials and methods used in carrying out the invention. The examples are not intended to limit the invention in any manner.

EXAMPLES 1–7

Materials and Methods

Calcium pectinate powder containing 4% calcium (food grade) was supplied by Genu-Copenhagen Pectin (Denmark). For the preparation of the coating suspension, calcium pectinate underwent fractionation using a sieve shaker (Levy Laboratory Equipment, LTD) and sieve of $149\mu$ (ASTM 100, 8" diameter) in order to obtain the fraction of $<149\mu$ particle size. Emcocel 90M (microcrystalline cellulose) (BP grade), Eudragit E 100 (Eud.E), ethylcellulose EC-N100 NF 0100 (EC), magnesium stearate (USP grade), cross polyvinylpyrrolidone (USP grade) (CPVP or Crospovidone), sodium diclofenac (BP grade) and sodium salicylate (USP grade) were purchased from Mendel, Rohm Pharma (Germany), Aqualon (Netherlands), Merck (Germany), Basf, Amoli Organics (India) and Merck (Germany), respectively. Pyridostigmine bromide was purchased from Orgasynth Industries (France). Ethyl alcohol was USP grade.

Granulation or a dry mixing method was used to prepare the blends for compressing in a tablet press. For dry mixing, all components of a formulation except magnesium stearate were mixed manually for 20 to 30 minutes in a polyethylene bag. Then magnesium stearate was added and the blend underwent additional mixing for about 2 to 3 minutes. Granulation will be described for each individual experiment.

Biconvex cores of 8 mm diameter were compressed automatically using a Korsh EK 0 single punch tablet press operated by the Erweka drive unit (AR 400). The weights of cores ranged between 220 to 300 mg depending on the core formulation. The hardness of the cores was tested using a Schleninger-2E Hardness Tester.

Biconvex cores of 9 mm diameter were also compressed automatically using a 15 punch Kilian RLS-15 tablet press fitted with a control unit type ROF-M. The hardness of the latter cores were measured using a Vankel VK200RC hardness tester.

The coating suspension was prepared by dissolving ethylcellulose (4% w/w) (8 g EC/200 g solution), in ethanol and then adding the calcium pectinate powder, to the desired weight ratio. The coating suspension was then kept stirred vigorously throughout the coating process to prevent the calcium pectinate deposition. The coating system consisted of a polyethylene pan coater (~12 cm diameter), an Heidolph (RZR 2051, electronic) driving motor, a peristaltic pump (Masterflex, Digital Console Drive, Cole-Palmer Instrument Company) and a nozzle composed from a "Y" connector tube fixed on one end to the air supply system and on the other to the coating suspension through the peristaltic pump and a stainless steel tip of 1.2 mm fixed at the head of the "Y" connector tube. The coating conditions such as the temperature, spraying rate (flow velocity of the suspension), air pressure (for the suspension spraying), air flow rate of the fan, and the rotation speed of the fan were kept constant throughout the coating process.

Dissolution studies were performed in intestinal fluid TS (phosphate buffer, pH 7.5 without enzymes) using a Vankel 7000 dissolution tester. One tablet was placed in 900 ml intestinal fluid TS and stirred by paddle at 50 RPM. The solutions were kept at 37° C. by a Vankel VK650A heater/circulator. Samples of 3 ml were taken using a Vankel VK8000 Autosampler, at intervals of 30 minutes up to 4 hours, followed by intervals of 1 hour up to 12 hours and finally intervals of 2 hours up to 20 hours. The actual determinations of the release of the drugs (dissolution results) from both coated and uncoated tablet were carried out using a HP 8452A Diode-Array Spectrophotometer. The drugs released from the coated and uncoated tablets were quantified using a calibration curve obtained from the standard solution, in intestinal solution TS, in the concentration range of 0–50 ppm.

EXAMPLE 1

Control of Burst Time by Weight (Thickness) of Coating

Tablets were produced using dry mixing of components. The formulation of the core is given in Table 1 (229-76A). The cores were of 8 mm diameter and had a hardness of 11–12 Kp. The uncoated core underwent disintegration in intestinal TS within several seconds releasing all the diclofenac. The cores were spray coated with different amounts of ethylcellulose:calcium pectinate (1:1 w/w). The results are shown in FIG. 1. An 8 mg coating per tablet gave a delay of 2 hours; 11 mg gave a delay of 4 hours; 17 mg a delay of 9 hours; 20 mg gave a delay of 12 hours. In each case the tablets fully disintegrated after the delay time.

Figure 2:
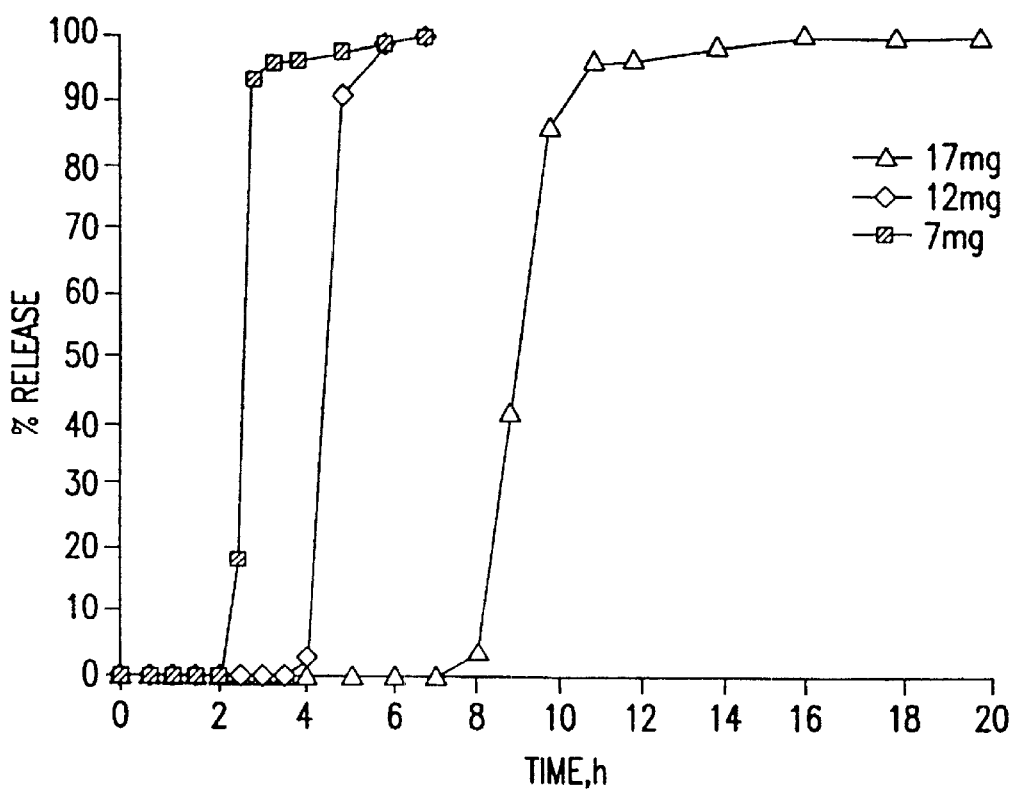
FIG. 2. Diclofenac release from tablets 229-99/A (5% CPV), coated with ethylcellulose/CaP (ratio 1:1).

Reducing the amount of Crospovidone to 5% (formulation 229-99A) gave essentially identical results. In FIG. 2, a 7 mg per tablet coating resulted in a delay of 2 hours; 12 mg resulted in a delay of 4 hours; and 17 mg resulted in a delay of 8 hours, before the drug was released in a burst. Formulations without Crospovidone did not provide a burst at all.

TABLE 1

Tablet Core Formulations

|  | 229 - 76A | 229 - 99A |
|---|---|---|
| Ca pectinate % | 59 | 59 |
| Emcocel % | 20 | 25 |
| CPVP % | 10 | 5 |
| Na-diclofenac % | 10 | 10 |
| Mg-Stearate % | 1 | 1 |
| Diameter mm | 8 | 8 |
| Hardness kp | 12 | 12 |
| Weight mg | 259.4 | 256.5 |

EXAMPLE 2

Effect of Tablet Hardness

Cores of tablets were made using the dry mixing method and compressed at different compression forces so as to create tablets with different hardness. The formulation was identical to that of 229-76A (Table 1). Tablet cores 229-93B gave a hardness of 11–13 kp while tablet cores 229-93A gave a hardness of 5–8 kp. The cores were spray coated with ethylcellulose:calcium pectinate at a weight/weight ratio of 1:1 as in Example 1.

Figure 3:
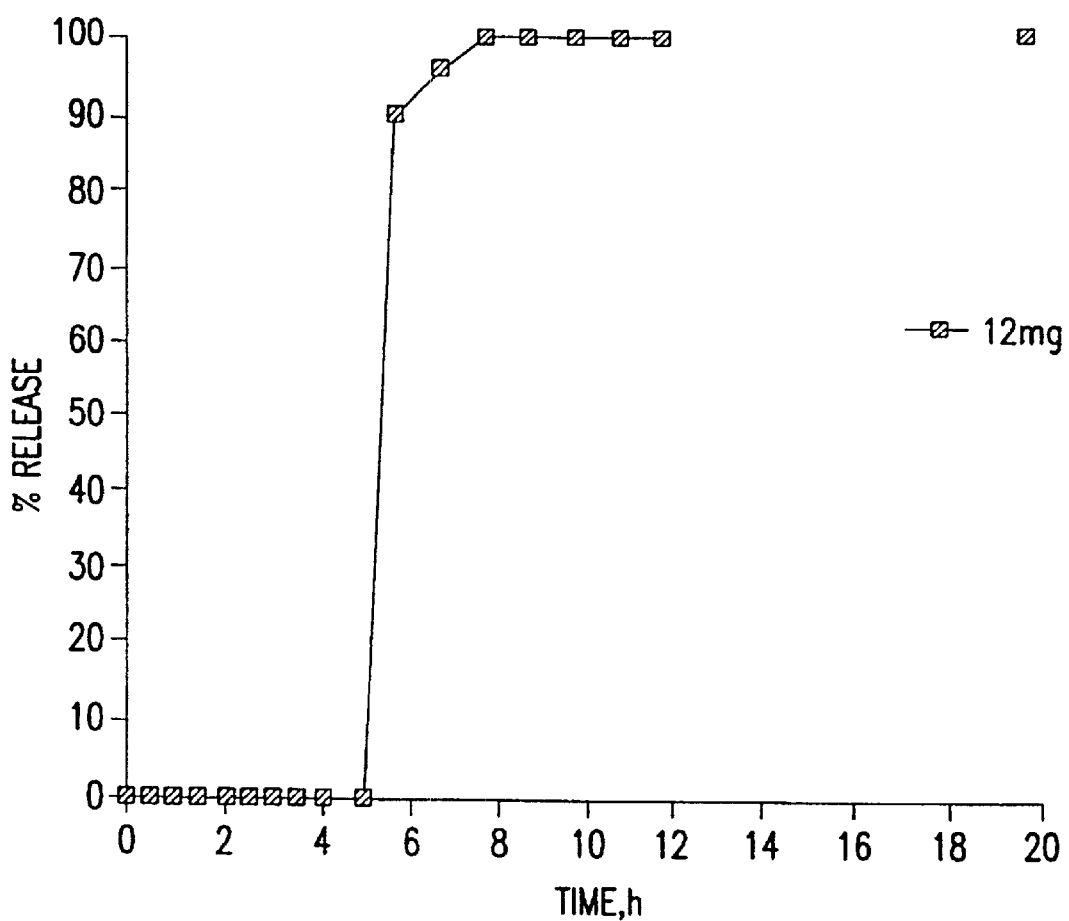
FIG. 3. Diclofenac release from tablets 229-93/B (hardness 11–13), coated with ethylcellolose/CaP (ratio 1:1).
Figure 4:
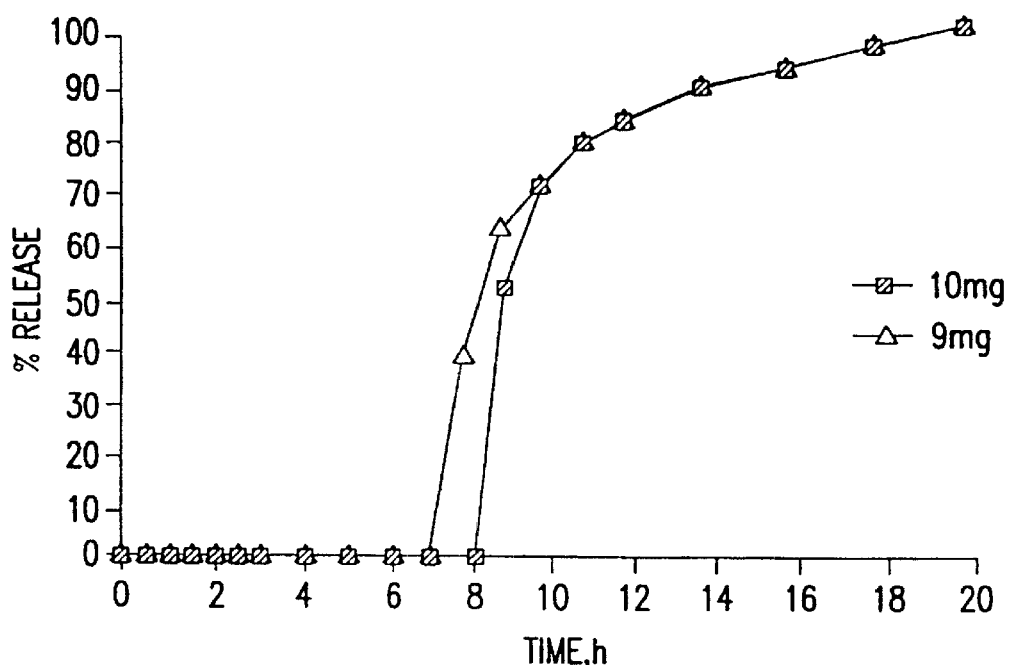
FIG. 4. Diclofenac release from tablets 229-93/A (hardness 5–6), coated with ethylcellulose/CaP (ratio 1:1).

Dissolution studies of coated tablets 229-93B, shown in FIG. 3 showed that a 12 mg coating per tablet gave a five hour delay before the drug was released in a burst. Coated tablets 229-93A did not show a burst of drug release. After a delay of 7–8 hours for a coating level of about 10 mg per tablet, the drug was released in a slow fashion (FIG. 4).

EXAMPLE 3

Effect of Hardness Enhancer (Emcocel) and Swelling Component (Calcium Pectinate)

Tablet cores were formulated without either Emcocel (formulation 229-99B, see Table 2), or without the swelling polymer calcium pectinate (formulation 229-99C, see Table 2). The tablets were produced under conditions of compression that gave them almost identical hardness.

TABLE 2

Tablet Core Formulations

|  | 229 - 99B | 229 - 99C |
|---|---|---|
| Ca pectinate % | 79 | 0 |
| Emcocel % | 0 | 79 |
| CPVP % | 10 | 10 |
| Na-diclofenac % | 10 | 10 |
| Mg-Stearate % | 1 | 1 |
| Diameter mm | 8 | 8 |
| Hardness kp | 12 | 12.5 |
| Weight mg | 255.4 | 224.1 |

The tablets were spray coated as in Example 1. In both cases, the tablets failed to show clean burst drug release. After a delay in drug release which is coating weight dependent, the drug was released in a burst of part of the drug content with the remainder being released slowly.

EXAMPLE 4

Effect of Drug Solubility on the System

Figure 5:
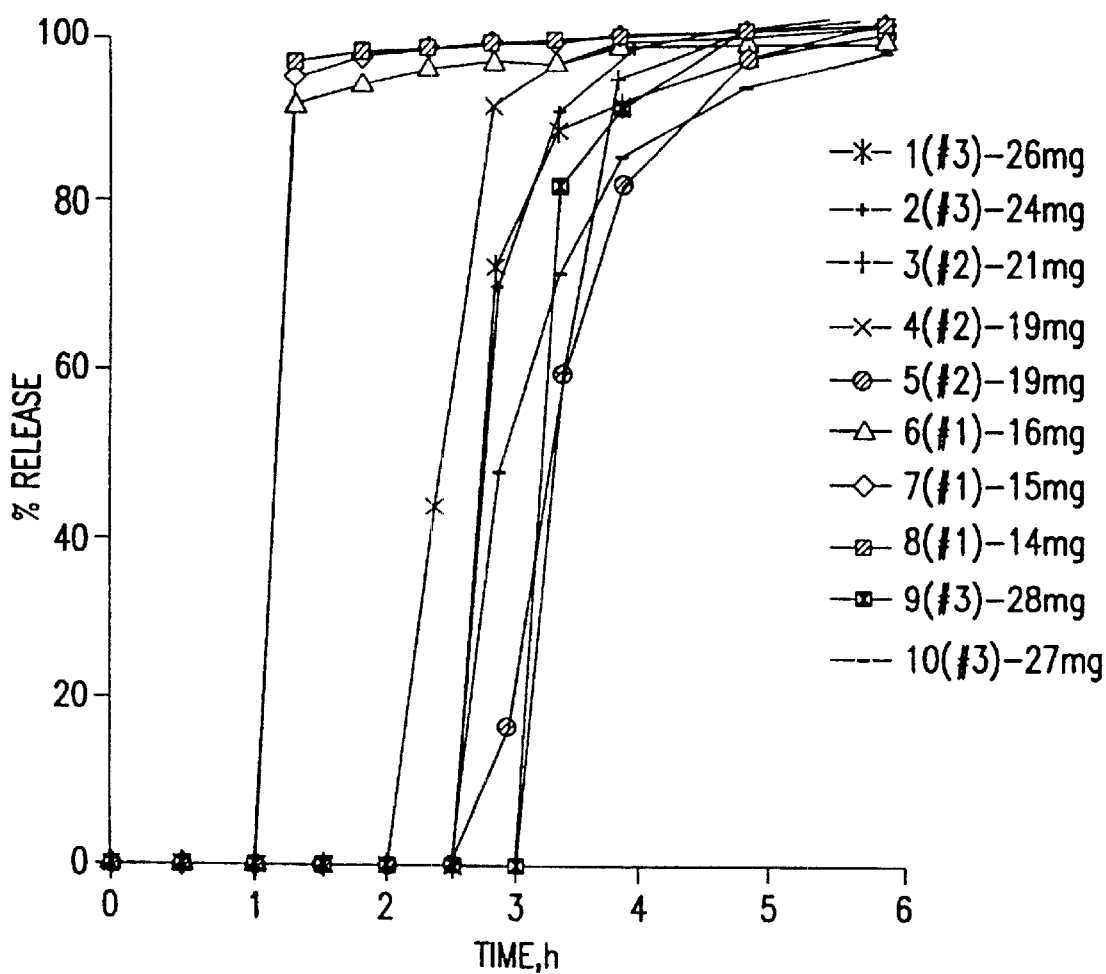
FIG. 5. Sodium salicylate release from tablets 229-113, coated with ethylcellulose/CaP (ratio 1:1).

Tablets were formulated using the highly soluble drug sodium salicylate instead of the partially soluble sodium diclofenac. The formulation used is described in Table 3. The tablets were spray coated with varying thicknesses of ethylcellulose: calcium pectinate (1:1) as in Example 1. FIG. 5 shows the results of the dissolution of these tablets in intestinal TS. The sodium salicylate, being more soluble, causes a quicker entry of water into the tablet bringing about a lowering in lag times for a given coating thickness (compare FIGS. 1 and 5). A 15 mg coating gave only one hour delay time, a 19 mg coating per tablet gave a two hour delay to the drug burst while a 24 mg coating gave a 2.5–3 hour delay. The osmotic drive for water entry is higher if the drug (a salt) is present in higher concentrations in the tablet. To prove this explanation we obtained similar results by formulating tablets of sodium diclofenac with the addition of calcium chloride (Table 3). These tablets were also spray coated as in Example 1. A coating of 19 mg gave a delay to burst of one hour when compared to a delay of 9 hours for a 17 mg coating seen in Example 1.

TABLE 3

Tablet Core Formulations

|  | 229 - 113 | 229 - 85B |
|---|---|---|
| Ca pectinate % | 59 | 59 |
| Emcocel % | 20 | 25 |
| CPVP % | 10 | 0 |
| $CaCl_2$ % | 0 | 5 |
| Na-diclofenac % | 0 | 10 |
| sodium salicylate % | 10 | 0 |
| Mg-Stearate % | 1 | 1 |
| Diameter mm | 8 | 8 |
| Hardness kp | 12 | 9.5 |
| Weight mg | 262.7 | 293.8 |

EXAMPLE 5

Cores Made with Granulation

Tablet cores were produced using a wet granulation method. The advantage of wet granulation over dry mixing is one of improved uniformity of content for low concentration, potent drugs, and of enhanced batch to batch reproducibility of the process. The granulation also improves the flowability of the powder and the hardness of the obtained tablets. The granulation was carried out as follows: 5.4 g of low viscosity ethylcellulose (e.g. nf-7) was dissolved in 90 ml ethanol, 265 g calcium pectinate was mixed with 15.75 g Crospovidone. The ethylcellulose solution was added slowly. The mixture was well mixed in a mortar and pestle and then dried at 60–65 degrees for 1.5 hours and at 40 degrees for overnight.

Low viscosity ethylcellulose (0.9 g) was dissolved in 15 ml ethanol. Diclofenac (45 g) was mixed with 2.7 g of Crospovidone and the ethylcellulose solution was added. The mixture was mixed with a mortar and pestle and dried overnight at 40 degrees. The granulates were then mixed with the remainder of th e components and tablets pressed.

TABLE 4

Tablet Core Formulation

|  | 263 - 129 |
| --- | --- |
| Ca pectinate Granulate % | 28.3 |
| Emcocel (90M) % | 50 |
| CPVP % | 10 |
| Na-diclofenac granulate % | 10.7 |
| Mg-Stearate % | 1 |
| Diameter mm | 7 |
| Hardness kp | 10 |
| Weight mg | 204.7 |

Figure 6:
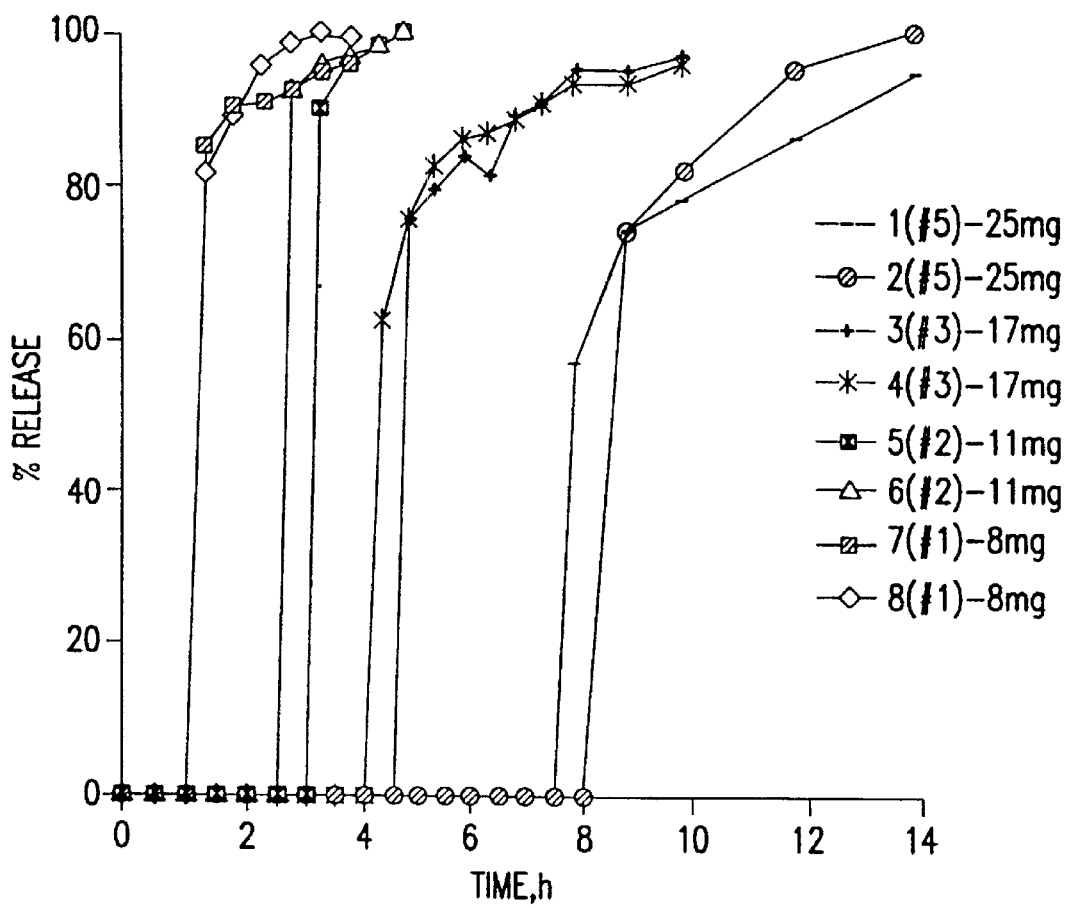
FIG. 6. Diclofenac release from tablets 263-129 (granulated CaP+CPV+EC, granulated diclofenac+CPV+EC; 50% Emcocel; D=7 mm), coated with ethocel 20/CaP (ratio 1:1).

The granulated calcium pectinate swells more efficiently than the calcium pectinate powder allowing a lowering of the percentage of calcium pectinate in the formulation. Tablets of formulation 263–129 (Table 4) were pressed and were coated with ethylcellulose; calcium pectinate (1:1). The dissolution was studied in intestinal TS. The results are shown in FIG. 6. Tablets coated with 8 mg per table gave a one hour delay to burst. Tablets coated with 11 mg gave a 2.5–3 hour delay. Tablets coated with 17 mg gave a delay of 4–4.5 hours. 25 mg gave a 7.5 to 8 hour delay.

EXAMPLE 6

Control of Burst Time by Changing EC: CaP Ratio

Figure 7:
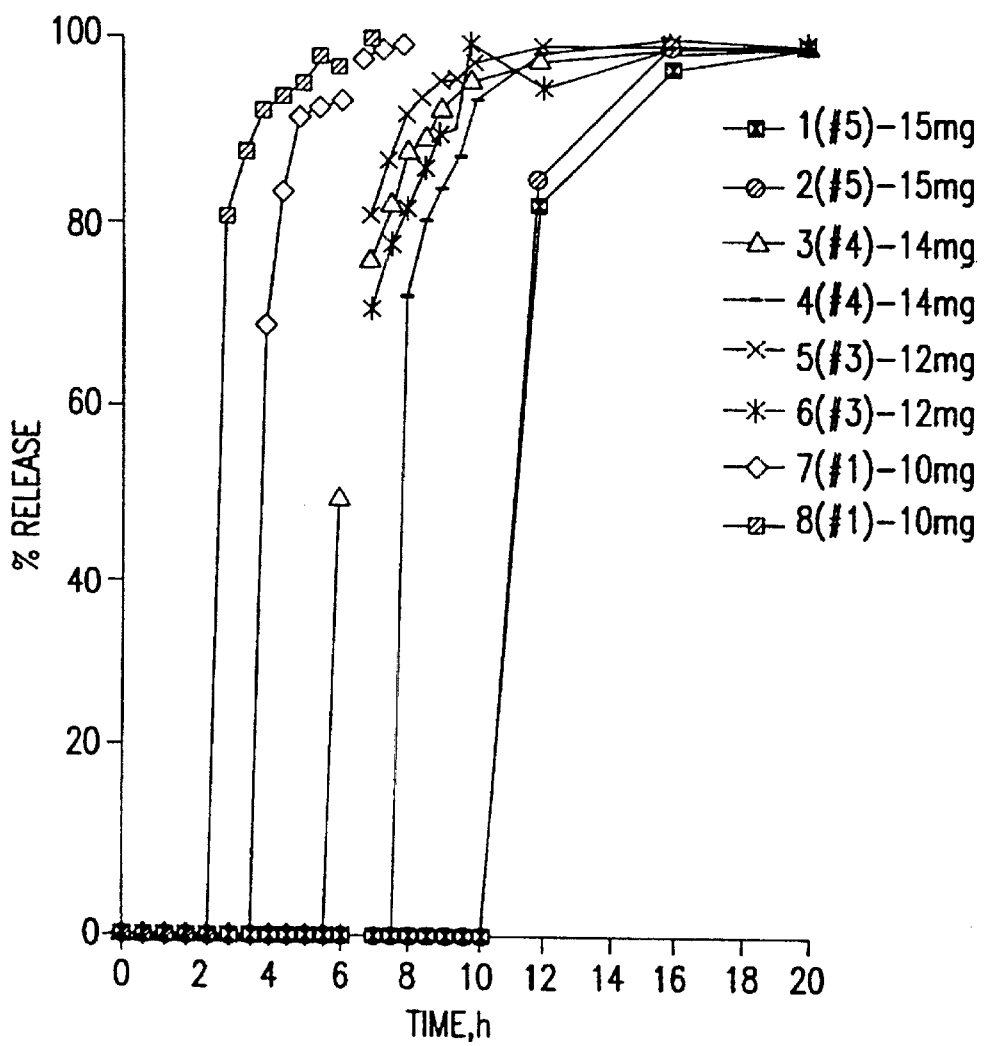
FIG. 7. Diclofenac release from tablets 263-123 (granulated CaP+CPV+EC, granulated diclofenac+CPV+EC; 50% Emcocel; D=7 mm), coated with ethocel 20/CaP (40% CaP).
Figure 8:
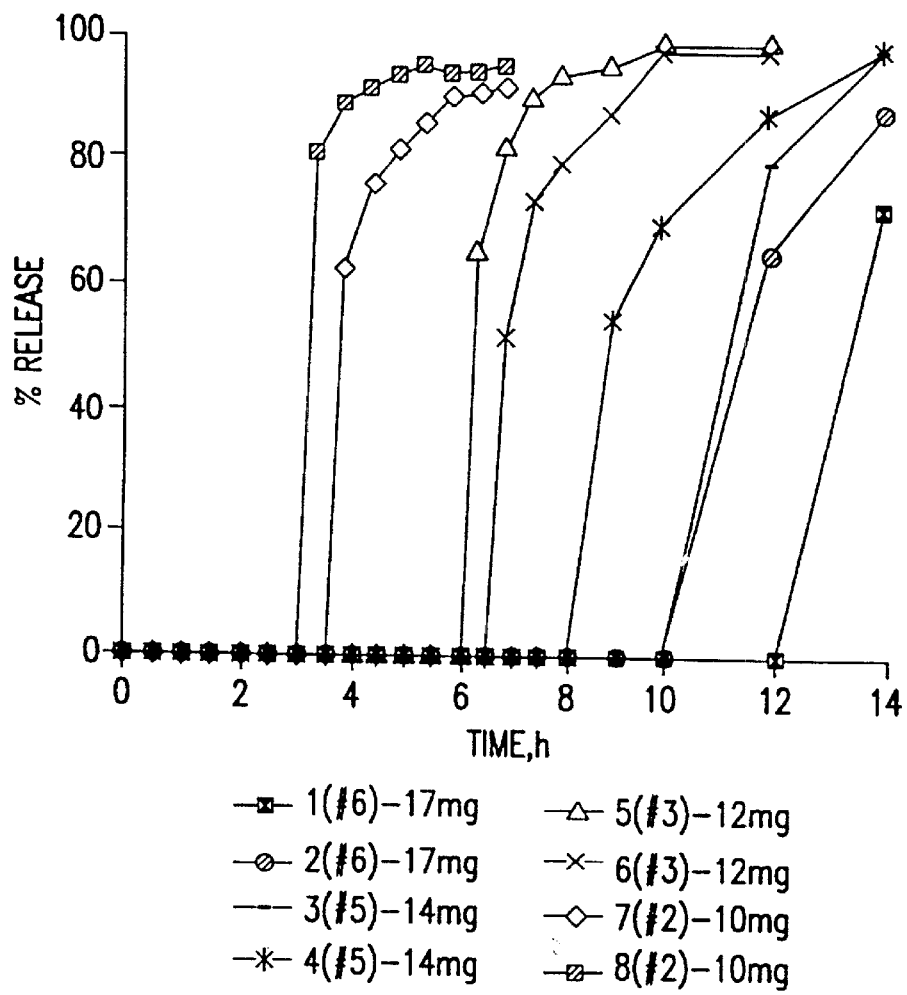
FIG. 8. Diclofenac release from tablets 263-123 (granulated CaP+CPV+EC, granulated diclofenac+CPV+EC; 50% Emcocel; D=7 mm), coated with ethocel 20/CaP (45% CaP).
Figure 9:
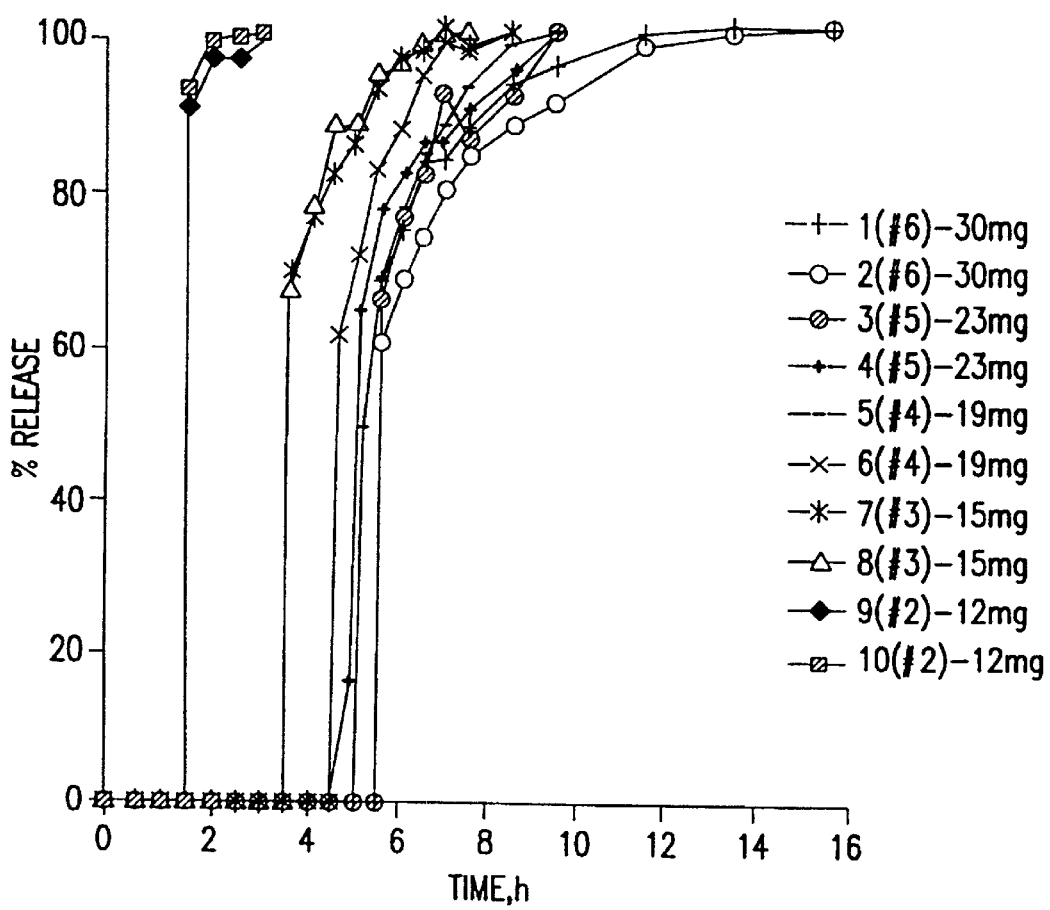
FIG. 9. Diclofenac release from tablets 263-123 (granulated CaP+CPV+EC, granulated diclofenac+CPV+EC; 50% Emcocel; D=7 mm), coated with ethocel 20/CaP (55% CaP).

An alternate method to coating thickness for controlling the time of delay to the burst release of the drug is by controlling the amount of calcium pectinate in the coating. Tablet cores of formulation 263-129 (Table 4) were coated with ethyl cellulose: calcium pectinate, with the content of calcium pectinate varying from 40% to 55%. FIG. 7 shows the results obtained for a coating containing 40% calcium pectinate, FIG. 8 for 45%, FIG. 29 for 50%, and FIG. 9 for 55%. The results show that for each coating type, the length of the delay to burst release of the drug can be controlled by the coating thickness. The results show that for a given coating thickness, there is a shorter delay when there is a higher percentage of calcium pectinate in the coating. Table 5 is a collection of the data for time of delay as a function of the % calcium pectinate.

TABLE 5

Delay of Drug Release as a Function of % CaP in Coating

| coating weight (mg) | % calcium pectinate | delay (hours) |
| --- | --- | --- |
| 12 | 40 | 7 |
| 12 | 45 | 6 |
| 11 | 50 | 3 |
| 12 | 55 | 1.5 |
| 15 | 40 | 10 |
| 14 | 45 | 9 |
| 17 | 50 | 4 |
| 15 | 55 | 3.5 |
| 25 | 50 | 8 |
| 23 | 55 | 5 |

Figure 10:
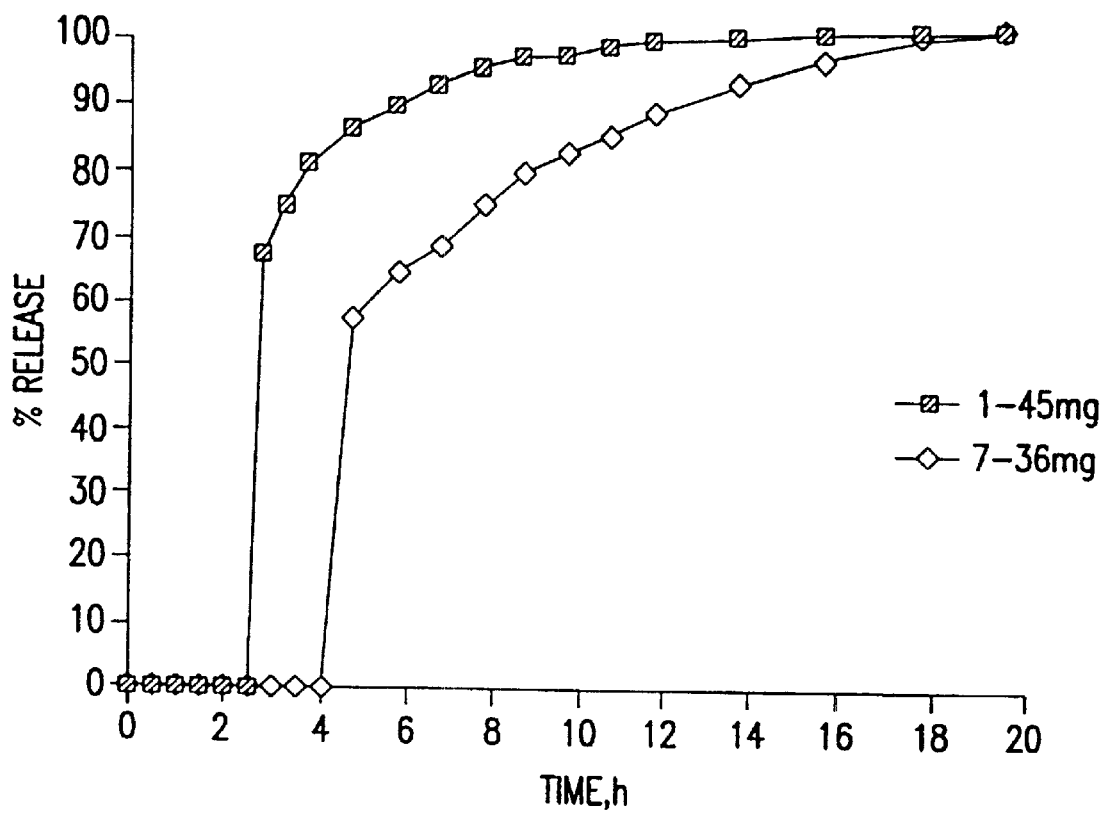
FIG. 10. Diclofenac release from tablets 229-76/A, coated with ethylcellulose/CaP (ratio 3:7).

Furthermore, tablets of formulation 229-76A (Table 1) were coated with films of calcium pectinate content of 50% and 70%. The results of the delay in drug release for 50% calcium pectinate in the coating is shown in FIG. 1, and for 70% in FIG. 10. With 70% calcium pectinate in the coating one needs a thick coating to be able to obtain a delay of 4 hours.

EXAMPLE 7

Pyridostigmine Bromide Delayed Total Release Tablets (Batch 350-80)

Eudragit S100, 1.6 grams, was dissolved in 10 ml ethanol. Pyridostigmine bromide, 2.5 gm, was added to the ethanol solution which was stirred until dissolution was complete. Calcium pectinate, 40 gm, was mixed with 2.4 gm of crosspovidone in a mortar and pestle while the ethanolic solution of eudragit S I 00 and pyridostigmine bromide was slowly added. After the mixture was well mixed, it was dried at 40° C. for 16 hours and then at 80° C. for 8 hours. The granules were sieved and the fraction <420µ was used.

The pyridostigmine-consisting granules were mixed with 1.4 gm of silicone dioxide, Aerosil R972, for 5 minutes to improve their flow properties. The mixture was transferred to a polyethylene bag to which 14 gm crosspovidone and 68.6 gm of microcrystalline cellulose, Emcocel 90 M, were added. The blend was mixed for 20–30 minutes. Magnesium stearate, 1.24 gm, was added and the blend mixed for another 2–3 minutes. Biconvex 8 mm cores were pressed automatically in a Wick Ges.mbh single punch tablet press. The cores weighed 250 mg and had a hardness of 10 Kp.

Figure 11:
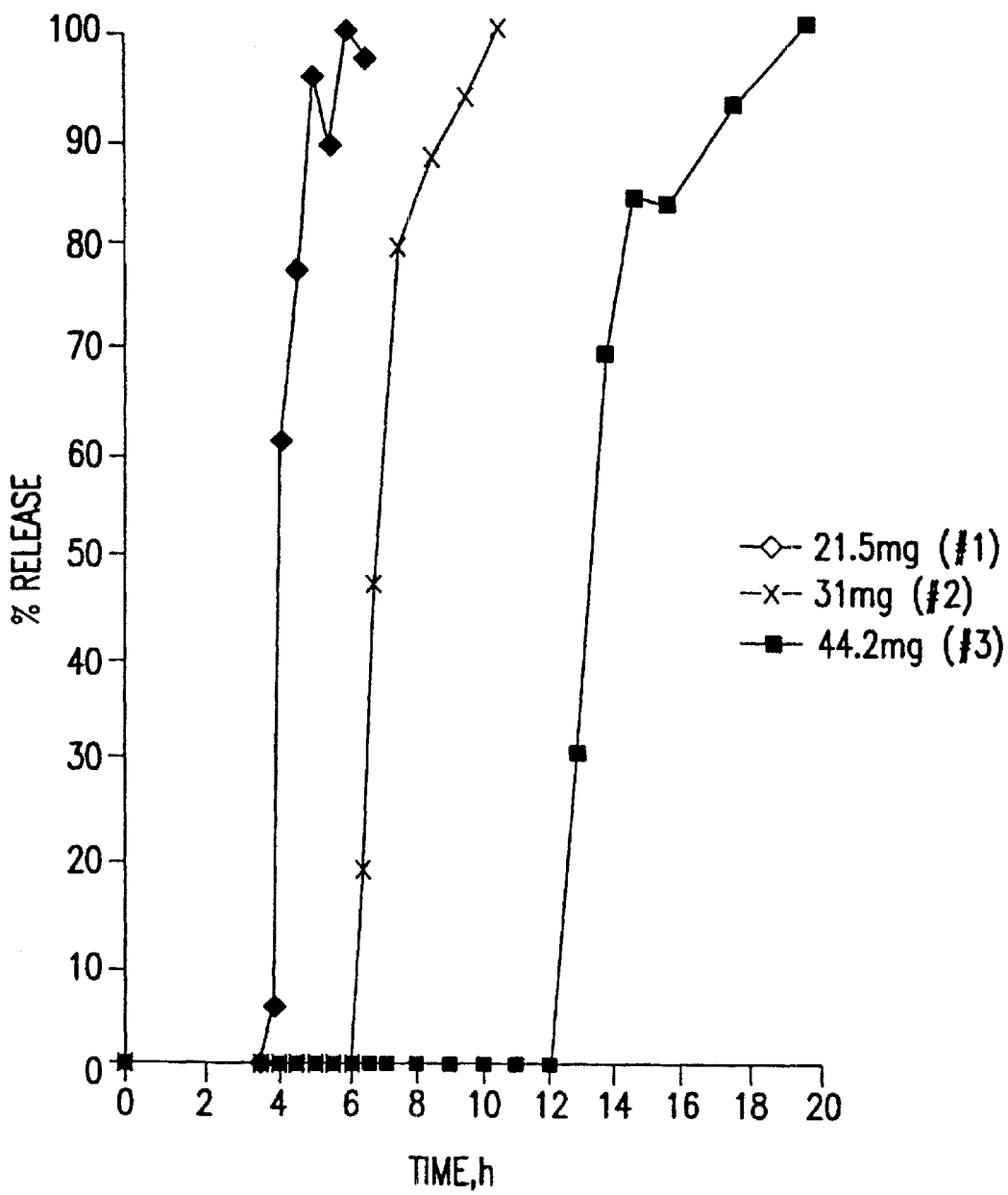
FIG. 11. Pyridostigmine Bromide Release from Tablets 350-80 (10 mg drug/tablet) coated with ethylcellulose/CaP (ratio 1:1).

The cores were coated with ethylcellulose: calcium pectinate 1:1 as described in the previous examples and were tested for their dissolution in intestinal TS solution. The results of the dissolution test are shown in FIG. 11. Tablets coated with 21.5 mg of coating gave a 4 hour delay until the immediate release of the drug content. Tablets coated with 31 mg gave a delay of 6.5 hours to the burst drug release, while those coated with 44.2 mg gave 13 hours to the burst delivery of the drug.

Discussion of Exemplary Material

Particles of calcium pectinate in a film of ethylcellulose are capable of dramatically altering the properties of the barrier film and give a new dimension to the control of release of soluble drugs from a matrix. A disintegrating tablet is incapable of targeting the delivery of a drug without a proper coating. This coating must prevent diffusion of drug from the tablet and control the intake of liquid into the core so as to control the time and place of tablet disintegration. The core must be capable of breaching the coating at a predetermined time and then disintegrating.

To allow for targeted delivery of soluble drugs a barrier to diffusion is necessary. This barrier must allow for control over the release of the drug to a timed point so that little or no drug is released before desired. The combination of non-water-soluble, but hydrophilic, particles in a hydrophobic coating allows for control of water entry into the tablet and thereby controlled time of disintegration. It has been shown that controlling several parameters (the percent of the particles, the particle size, the film thickness, the identity of the polymer, the identity of the particulate material, and the composition of the core), the time of release of drug from an immediate delivery disintegrating tablet can be controlled. The general trend is as follows:

1. Composition of the core: The more soluble components, whether drug or salts, in the core, the higher the osmotic pressure of the liquid across the membrane, and the faster the liquid crosses through the channels in the membrane into the core.
2. Percent of particles: The higher the percent of hydrophilic, non-soluble particulates embedded in the hydrophobic polymer, the earlier the release of the drug. This is thought to be because more channels are formed through which the liquid can enter the core.
3. Particle size of the particle: The smaller the particle size, the faster the release of drug for a given percent of particles. The smaller particles means that there are numerically more particles for a given weight percentage. The particles also have a larger total surface area so that more interaction among the particles embedded in the film is possible, possibly leading to more channels for liquid entry into the core.
4. Film thickness: The thicker the film, the slower the release of the soluble drug. Thicker films require a longer time for swelling of the hydrophilic insoluble particles across the entire cross section of the hydrophobic barrier film.
5. Identity of the polymer and particulate: The more hydrophobic the polymer, the longer the release time when all other parameters are kept the same. It will take longer for the hydrophilic channels to form when the polymer is more hydrophobic. The more hydrophilic and swellable the particulate, the faster the release when all other parameters are kept the same, since liquid enters the core through the swollen hydrophilic channels causing the core to swell and burst the coating. The more the particulate swells the larger the channels. The more hydrophilic the particulate, the faster the channels form and the more efficient they are at allowing the liquid to diffuse through them.

It is important to have many parameters that allow control of the immediate total release of a drug since each drug—matrix combination is unique and the characteristics of the various sites in the gastrointestinal tract are also unique. The present invention allows one to tailor the design of the film coating to the needs of any system.

Having now fully described the invention, it would be understood by those with skill in the art that the invention may be performed within a wide and equivalent range of conditions, parameters, and the like, without affecting the spirit or scope of the invention or any embodiment therefore. All references cited herein are incorporated herein fully by reference for their relevant teachings.

What is claimed is:

1. A delivery device for immediate localized release of a desired agent in the gastrointestinal tract of an animal, said device comprising:

a. a core comprising said agent, a core material that swells when exposed to an aqueous liquid, and a disintegrant; and b. a rigid coating surrounding said core that disintegrates and bursts when said core swells, said coating having an outer surface, said coating comprising water-insoluble hydrophilic particulate matter embedded in a water-insoluble carrier, wherein said particulate matter forms channels in said coating that interconnect said core with said outer surface of said coating in the presence of said liquid, and wherein said core disintegrates after said coating bursts, wherein said rigidity of said coating is such that the area under the stress-strain curve of units of energy per area of coating where said coating does not tear is at least about 0.009.

2. The device of claim 1 wherein said core is selected from the group consisting of a tablet, capsule, and pellet.

3. The device of claim 1 wherein said water-insoluble carrier is selected from the group consisting of: a dimethylaminoethlyacrylate/ethylmethacrylate copolymer, a copolymer based on acrylic and methacrylic acid esters with a low content of quaternary ammonium groups wherein the molar ratio of the ammonium groups to the remaining neutral (meth)acrylic acid esters is about 1:20; an ethylmethacrylate/chlorotrimethylammoniumethyl methacrylate copolymer, a copolymer based on acrylic and methacrylic acid esters with a low content of quaternary ammonium groups wherein the molar ratio of the ammonium groups to the remaining neutral (meth)acrylic acid esters is 1:40; ethylcellulose; shellac; and zein.

4. The device of claim 1 wherein said outer surface of said coating (b) is further coated with an enteric coating.

5. The device of claim 1 wherein said swellable core material is selected from the group consisting of polysaccharide, cross-linked polyacrylic acid, and modified cellulose.

6. The device of claim 5 wherein said polysaccharide is selected from the group consisting of insoluble metal salts or cross-linked derivatives of alginate, pectin, xantham gum, guar gum, tragacanth gum, and locust bean gum, carrageenan, starch, microcrystalline starch, microcrystalline cellulose, metal salts thereof, and covalently crosslinked derivatives thereof.

7. The device of claim 5 wherein said modified cellulose is selected from the group consisting of cross-linked derivatives of hydroxypropylcellulose, hydroxyethylcellulose, methylcellulose and carboxymethylcellulose and metal salts of carboxymethylcellulose.

8. The device of claim 1 wherein said particulate matter comprises a polymer selected from the group consisting of a water-insoluble polysaccharide, a water-insoluble cross-linked polysaccharide, a water-insoluble polysaccharide metal salt, a water-insoluble cross-linked protein, a water-insoluble cross-linked peptide, water insoluble protein: polysaccharide complex, a water insoluble peptide: polysaccharide complex, a polysaccharide or a protein or peptide rendered insoluble by interaction with a poly-cation or poly-anion and a water-insoluble cross-linked hydrophilic polymer in dried powder form.

9. The device of claim 8 wherein said polysaccharide is selected from the group consisting of an insoluble metal salt of pectin, xantham gum, carrageenan, tragacanth gum, locust bean gum, and alginic acid; an insoluble crosslinked derivative of xantham gum, guar gum, dextran, carrageenan, tragacanth gum, locust bean gum, pectin, starch, hydroxypropylcellulose, hydroxyethylcellulose, hydroxypropylmethylcellulose, carboxymethyl-cellulose and alginic acid, cellulose, microcrystalline cellulose, insoluble starch and microcrystalline starch.

10. The device of claim 9 wherein said insoluble metal salt of alginic acid is selected from the group consisting of calcium alginate, zinc alginate, aluminum alginate, ferric alginate, and ferrous alginate.

11. The device of claim 9 wherein said insoluble metal salt of pectin is selected from the group consisting of calcium pectinate, zinc pectinate, aluminum pectinate, ferric pectinate, and ferrous pectinate.

12. The device of claim 8 wherein said cross-linking is by a cross-linking agent selected from the group consisting of formaldehyde, glutaraldehyde, epichlorhydrin, diacid chloride, diacid anhydride, diisocyanates, diamines and borax.

13. The device of claim 8 wherein said water insoluble cross-linked protein is selected from the group consisting of glutaraldehyde-cross-linked hydrolyzed gelatin, formaldehyde-cross-linked hydrolyzed gelatin, glutaraldehyde-cross-linked gelatin, formaldehyde-cross-linked gelatin, glutaraldehyde-cross-linked collagen and formaldehyde-cross-linked collagen.

14. The device of claim 8 wherein said water-insoluble cross-linked hydrophilic polymer is a carbomer.

15. The device of claim 8 wherein said water-insoluble cross-linked hydrophilic polymer is Crospovidone.

16. The device of claim 4 wherein said water-insoluble carrier is ethylcellulose, said water-insoluble hydrophilic particulate is calcium pectinate, and said enteric coating is a methacrylic acid/methylmethacrylate or ethylacrylate anionic copolymer based on i) methacrylic acid and methylmethacrylate or ii) on methacrylic acid and ethylacrylate, wherein the ratio of free carboxyl groups to the ester groups is approximately 1:1.

17. The device of claim 1, wherein said desired agent is a diagnostic or therapeutic agent.

18. The device of claim 17, wherein said therapeutic agent is selected from the group consisting of a non-steroidal anti-inflammatory agent (NSAID), a steroid, a contraceptive, a steroidal hormone, an immunosuppressant, a bronchodialator, an anti-anginal, an anti-hypertensive, an anti-spasmodic agent, an anti-colitis agent, an anti-arrhythmia agent, an anti-neoplastic agent, a protein, a peptide, a hormone, a vaccine, an anticoagulant, an anti-migrane agent, glibenclamide, a 5-hydroxytryptamine type$_{1A}$ receptor agonist, a 5HT$_3$ antagonist, metkepyhamid, menthol, an antibiotic, a prostaglandin E$_1$ analogue, a prokinetic drug, a cholinergic agonist, a dopamine antagonist, and a reversible inhibitor of acetylcholinesterase.

19. The device of claim 18 wherein said therapeutic agent is selected from the group consisting of a prokinetic drug, a cholinergic agonist, and a reversible inhibitor of acetylcholinesterase.

20. The device of claim 19, wherein said therapeutic agent is said reversible inhibitor of acetylcholinesterase.

21. The device of claim 20 wherein said reversible inhibitor of acetylcholinesterase is selected from the group consisting of pyridostigmine bromide, neostigmine, neostigmine bromide, neostigmine methylsulfate, physostigmine, physostigmine salicylate and physostigmine sulfate.

22. The device of claim 18, wherein said therapeutic agent is a non-steroidal anti-inflammatory agent.

23. The device of claim 22, wherein said non-steroidal anti-inflammatory agent is selected from the group consisting of diclofenac, flurbiprofen and sulindac.

24. The device of claim 17, wherein said therapeutic active agent is useful for the treatment of colitis, Crohn's disease, irritable bowel syndrome, gastritis, pancreatitis, hypertension, angina, arthritis, rheumatoid arthritis, asthma, arrythmia, local spasmolytic action, ulceration of the mucosa, diarrhea, constipation, polpys, carcinoma, cysts, an infectious disorder or a parasitic disorder.

25. A method of delivering a desired agent to the gastrointestinal tract of an animal, wherein said method comprises oral administration of the drug delivery device of any one of claims 1–16.

26. The method of claim 24 wherein said agent is a diagnostic agent or a therapeutic agent.

27. The method of claim 25 wherein said agent is said diagnostic agent.

28. The method of claim 25 wherein said agent is said therapeutic agent.

29. The method of claim 24 wherein the portion of the gastrointestinal tract wherein said agent is released is selected from the group consisting of the stomach, the small intestine, the colon, and the rectum.

30. The method of claim 24 wherein said animal has been diagnosed as having a condition selected from the group consisting of colitis, Crohn's disease, irritable bowel syndrome, gastritis, pancreatitis, hypertension, angina, arthritis, rheumatoid arthritis, asthma, arrythmia, local spasmolytic action, ulceration of the mucosa, diarrhea, constipation, polyps, carcinoma, cysts, infectious disorders, and parasitic disorders.

31. The method of claim 29 wherein said condition is constipation.

32. A method of delivering a desired agent to the gastrointestinal tract of an animal, wherein said method comprises oral administration of the delivery device of claim 17.

33. The method of claim 29 wherein said agent is selected from the group consisting of a prokinetic drug, a cholinergic agonist, and a reversible inhibitor of acetylcholinesterase.

34. The method of claim 32 wherein said agent is a reversible inhibitor of acetylcholinesterase.

35. The method of claim 33 wherein said reversible inhibitor of acetylcholinesterase is selected from the group consisting of pyridostigmine bromide, neostigmine, neostigmine bromide, neostigmine methylsulfate. physostigmine, physostigmine salicylate, or physostigmine sulfate.

36. The method of claim 29 wherein said agent is a non-steroidal anti-inflammatory agent.

37. The method of claim 35 wherein said non-steroidal anti-inflammatory agent is selected from the group consisting of diclofenac, flurbiprofen and sulindac.

38. The delivery device of claim 1, further comprising a high osmotic gradient across said coating for enhancing uptake of said liquid to said core.

39. The delivery device of claim 38, wherein said core contains a water soluble salt and said coating contains a water soluble salt, wherein a concentration of said water soluble salt in said core is higher than a concentration of said water soluble salt in said coating.

40. The delivery device of claim 1, wherein said core further comprises a hardness enhancer.

41. The delivery device of claim 1, wherein said core material comprises a swellable, non-hydrogel forming water insoluble polymer.

42. The delivery device of claim 1, wherein said relative rigidity of said coating is such that the area under the stress-strain curve of units of energy per area of coating where said coating does not tear is in a range of from about 0.009 to about 0.21 MPa.

43. A delivery device for immediate localized release of a desired agent in the gastrointestinal tract of an animal, said device comprising:

(a) a core comprising said agent, a core material that swells when exposed to an aqueous liquid, wherein said core material comprises water-insoluble matter and a disintegrant; and (b) a coating surrounding said core that disintegrates and bursts when said core swells, said coating having an outer surface, said coating comprising water-insoluble hydrophilic particulate matter embedded in a water-insoluble carrier, wherein said particulate matter forms channels in said coating that interconnect said core with said outer surface of said coating in the presence of said liquid, and wherein said core disintegrates after said coating bursts;

wherein an osmotic gradient is present across said coating such that said core imbibes liquid due to said water-insoluble matter.

44. A delivery device for immediate localized release of a desired agent in the gastrointestinal tract of an animal, said device comprising:

(a) a core comprising said agent, a core material that swells when exposed to an aqueous liquid, a hardness enhancer, and a disintegrant; and (b) a coating surrounding said core that disintegrates and bursts when said core swells, said coating having an outer surface, said coating comprising water-insoluble hydrophilic particulate matter embedded in a water-insoluble carrier, wherein said particulate matter forms channels in said coating that interconnect said core with said outer surface of said coating in the presence of said liquid, and wherein said core disintegrates after said coating bursts.

\* \* \* \* \*

UNITED STATES PATENT AND TRADEMARK OFFICE
CERTIFICATE OF CORRECTION

PATENT NO.    : 6,531,152 B1
DATED         : March 11, 2003
INVENTOR(S)   : Lerner et al.

It is certified that error appears in the above-identified patent and that said Letters Patent is hereby corrected as shown below:

<u>Title page, Item [54] and Column 1, lines 1-3,</u>
The title should read:
-- DELAYED TOTAL RELEASE GASTROINTESTINAL DRUG DELIVERY SYSTEM --

Signed and Sealed this

Ninth Day of September, 2003

JAMES E. ROGAN
*Director of the United States Patent and Trademark Office*